US012195755B2

(12) United States Patent
Shukla et al.

(10) Patent No.: US 12,195,755 B2
(45) Date of Patent: Jan. 14, 2025

(54) PLACENTAL LIPID BILAYER FOR CELL-FREE MOLECULAR INTERACTION STUDIES

(71) Applicant: BROWN UNIVERSITY, Providence, RI (US)

(72) Inventors: Anita Shukla, Providence, RI (US); Christina Bailey-Hytholt, Providence, RI (US); Anubhav Tripathi, Northborough, MA (US)

(73) Assignee: BROWN UNIVERSITY, Providence, RI (US)

( * ) Notice: Subject to any disclaimer, the term of this patent is extended or adjusted under 35 U.S.C. 154(b) by 1147 days.

(21) Appl. No.: 16/822,994

(22) Filed: Mar. 18, 2020

(65) Prior Publication Data

US 2020/0370008 A1   Nov. 26, 2020

Related U.S. Application Data

(60) Provisional application No. 62/976,882, filed on Feb. 14, 2020, provisional application No. 62/905,756, filed on Sep. 25, 2019, provisional application No. 62/850,188, filed on May 20, 2019.

(51) Int. Cl.
| | |
|---|---|
| *C12N 5/073* | (2010.01) |
| *A61K 9/16* | (2006.01) |
| *A61K 35/50* | (2015.01) |
| *A61K 49/18* | (2006.01) |

(Continued)

(52) U.S. Cl.
CPC .......... *C12N 5/0605* (2013.01); *A61K 9/1617* (2013.01); *A61K 35/50* (2013.01); *A61K 49/1839* (2013.01); *C07K 14/4715* (2013.01); *G01N 33/5014* (2013.01); *C12N 2506/025* (2013.01); *G01N 2405/04* (2013.01)

(58) Field of Classification Search
CPC ............ C12N 5/0605; C12N 2506/025; A61K 9/1617; A61K 35/50; A61K 49/1839; C07K 14/4715; G01N 33/5014; G01N 2405/04; G01N 33/92
USPC ........................................... 435/1.1; 424/583
See application file for complete search history.

(56) References Cited

U.S. PATENT DOCUMENTS

| | | |
|---|---|---|
| 4,535,156 A | 8/1985 | Blumbach et al. |
| 4,883,868 A | 11/1989 | Nakagawa et al. |
| 5,233,035 A | 8/1993 | Hara et al. |

(Continued)

FOREIGN PATENT DOCUMENTS

| | | |
|---|---|---|
| AU | 5735500 A | 1/2001 |
| CN | 1969830 A | 5/2007 |

(Continued)

OTHER PUBLICATIONS

Lipid domain structure correlated with membrane protein function in placental microvillus vesicles. Biochemistry 26, 446-454 (Year: 1987).*

(Continued)

*Primary Examiner* — Christopher L Chin
(74) *Attorney, Agent, or Firm* — ADLER POLLOCK & SHEEHAN P.C.

(57) ABSTRACT

The invention provides a lipid bilayer mimicking the lipid composition of the placenta. The lipid composition provides an in vitro placenta model using the lipid composition of the placental cell membrane.

10 Claims, 13 Drawing Sheets

(51) Int. Cl.
*C07K 14/47* (2006.01)
*G01N 33/50* (2006.01)

(56) References Cited

U.S. PATENT DOCUMENTS

| | | |
|---|---|---|
| 5,571,666 A | 11/1996 | Floyd et al. |
| 5,626,863 A | 5/1997 | Hubbell et al. |
| 5,965,156 A | 10/1999 | Proffitt et al. |
| 6,153,252 A | 11/2000 | Hossainy et al. |
| 6,514,535 B2 | 2/2003 | Marchant |
| 6,641,831 B1 | 11/2003 | Schierholz |
| 6,787,179 B2 | 9/2004 | Timm et al. |
| 6,818,018 B1 | 11/2004 | Sawhney |
| 7,323,303 B2 | 1/2008 | Wong et al. |
| 7,396,926 B2 | 7/2008 | Tsien et al. |
| 7,541,048 B2 | 6/2009 | Dewitt et al. |
| 7,632,657 B2 | 12/2009 | Rambach et al. |
| 7,914,841 B2 | 3/2011 | Eells et al. |
| 8,092,784 B2 | 1/2012 | Mao et al. |
| 8,097,434 B2 | 1/2012 | Yang-Woytowitz et al. |
| 8,209,992 B2 | 7/2012 | Alden |
| 8,389,234 B2 | 3/2013 | Yang-Woytowitz et al. |
| 8,414,909 B2 | 4/2013 | Wang |
| 8,586,325 B2 | 11/2013 | Mao et al. |
| 8,679,520 B2 | 3/2014 | Horres et al. |
| 8,778,627 B2 | 7/2014 | Mao et al. |
| 8,784,862 B2 | 7/2014 | Horres et al. |
| 8,802,387 B2 | 8/2014 | Xing et al. |
| 8,883,772 B2 | 11/2014 | Sutton et al. |
| 8,916,227 B2 | 12/2014 | Horres et al. |
| 8,986,781 B2 | 3/2015 | Chen et al. |
| 9,012,167 B2 | 4/2015 | Dallenne et al. |
| 9,085,794 B2 | 7/2015 | Yang-Woytowitz et al. |
| 9,138,490 B2 | 9/2015 | Cirillo et al. |
| 9,192,697 B2 | 11/2015 | Hoffmann et al. |
| 9,283,194 B2 | 3/2016 | Tang et al. |
| 9,441,261 B2 | 9/2016 | Cirillo et al. |
| 9,453,032 B2 | 9/2016 | Sutton et al. |
| 9,476,087 B2 | 10/2016 | Xing et al. |
| 9,504,643 B2 | 11/2016 | Tice et al. |
| 9,539,273 B2 | 1/2017 | Meehan et al. |
| 9,566,247 B2 | 2/2017 | Koo et al. |
| 9,592,299 B2 | 3/2017 | Sershen et al. |
| 9,597,407 B2 | 3/2017 | Eckert et al. |
| 9,603,883 B2 | 3/2017 | Huang et al. |
| 9,670,476 B2 | 6/2017 | Mao et al. |
| 9,677,112 B2 | 6/2017 | Rao et al. |
| 9,689,021 B2 | 6/2017 | Brans et al. |
| 9,694,081 B2 | 7/2017 | Burdick et al. |
| 9,809,605 B1 | 11/2017 | Sutton et al. |
| 9,828,622 B2 | 11/2017 | Hasan et al. |
| 9,834,681 B2 | 12/2017 | Rao et al. |
| 9,862,729 B2 | 1/2018 | Sutton et al. |
| 9,874,568 B2 | 1/2018 | Charretier et al. |
| 9,902,989 B2 | 2/2018 | Yang-Woytowitz et al. |
| 9,956,252 B2 | 5/2018 | Tseng et al. |
| 10,000,491 B2 | 6/2018 | Abe et al. |
| 10,000,492 B2 | 6/2018 | Abe et al. |
| 10,000,509 B2 | 6/2018 | Sutton et al. |
| 10,041,105 B2 | 8/2018 | Li |
| 10,175,239 B2 | 1/2019 | Cirillo et al. |
| 10,239,890 B2 | 3/2019 | Sutton et al. |
| 10,293,085 B2 | 5/2019 | Orlowski |
| 2003/0040501 A1 | 2/2003 | Newman et al. |
| 2004/0022853 A1 | 2/2004 | Ashton et al. |
| 2005/0013854 A1 | 1/2005 | Mannino et al. |
| 2008/0255498 A1 | 10/2008 | Houle |
| 2008/0261960 A1 | 10/2008 | Brown et al. |
| 2009/0238867 A1 | 9/2009 | Jenkins et al. |
| 2010/0129432 A1 | 5/2010 | Chen et al. |
| 2010/0147763 A1 | 6/2010 | Tsou et al. |
| 2011/0076319 A1 | 3/2011 | Orlowski et al. |
| 2011/0150961 A1 | 6/2011 | Perry et al. |
| 2012/0009834 A1 | 1/2012 | Augustyniak et al. |
| 2013/0003061 A1 | 1/2013 | Amin et al. |
| 2013/0103139 A1 | 4/2013 | Hoffmann et al. |
| 2014/0199241 A1 | 7/2014 | Yedgar |
| 2014/0219917 A1 | 8/2014 | Murthy et al. |
| 2014/0349886 A1 | 11/2014 | Lee et al. |
| 2016/0058864 A1 | 3/2016 | Meehan et al. |
| 2016/0082159 A1 | 3/2016 | Orlowski |
| 2016/0199351 A1 | 7/2016 | Rappleye et al. |
| 2016/0333027 A1 | 11/2016 | Rao et al. |
| 2016/0376629 A1 | 12/2016 | Cirillo et al. |
| 2017/0189392 A1 | 7/2017 | Tong et al. |
| 2017/0354741 A1 | 12/2017 | Ofner, III et al. |
| 2018/0094139 A1 | 4/2018 | Rao et al. |
| 2018/0094292 A1 | 4/2018 | Hasan et al. |
| 2018/0105862 A1 | 4/2018 | Dequaire-Rochelet et al. |
| 2018/0156796 A1 | 6/2018 | Geisberg |
| 2018/0186939 A1 | 7/2018 | Blanchemain et al. |
| 2018/0282778 A1 | 10/2018 | Nordmann et al. |
| 2018/0334701 A1 | 11/2018 | Yang-Woytowitz et al. |
| 2019/0101538 A1 | 4/2019 | Cirillo et al. |
| 2019/0307904 A1 | 10/2019 | Ballamy |
| 2019/0321520 A1 | 10/2019 | Weaver et al. |
| 2022/0229065 A1 | 7/2022 | Rai et al. |
| 2023/0190761 A1 | 6/2023 | Brader et al. |

FOREIGN PATENT DOCUMENTS

| | | | |
|---|---|---|---|
| CN | 110613686 A | 12/2019 | |
| CN | 110694136 A | 1/2020 | |
| CN | 109580575 B | 7/2020 | |
| CN | 112697766 B | 4/2022 | |
| CN | 217542886 U | 10/2022 | |
| CN | 113075193 B | 12/2022 | |
| CN | 113912626 B | 3/2023 | |
| DE | 102004046244 A1 | 3/2006 | |
| DE | 102005039126 A1 | 2/2007 | |
| EP | 0034759 B1 | 1/1986 | |
| EP | 0745390 A2 | 12/1996 | |
| EP | 2285381 B1 | 12/2015 | |
| EP | 3058958 B1 | 9/2018 | |
| EP | 3442612 A1 | 2/2019 | |
| EP | 3380825 B1 | 9/2020 | |
| JP | 2007118003 A | 5/2007 | |
| WO | 0100247 A9 | 8/2002 | |
| WO | 2009005798 A2 | 1/2009 | |
| WO | 2014008875 A1 | 1/2014 | |
| WO | 2014122152 A1 | 8/2014 | |
| WO | 2016066718 A1 | 5/2016 | |
| WO | WO-2016154319 A1 * | 9/2016 | ........... B01D 63/088 |
| WO | 2017021023 A1 | 2/2017 | |
| WO | 2017037232 A1 | 3/2017 | |
| WO | 2017053778 A1 | 3/2017 | |
| WO | WO-2017147049 A1 * | 8/2017 | ........... A61K 31/685 |
| WO | 2018204782 A1 | 11/2018 | |
| WO | 2018213352 A1 | 11/2018 | |
| WO | 2020131192 A2 | 6/2020 | |
| WO | 2020146514 A1 | 7/2020 | |
| WO | 2021130242 A1 | 7/2021 | |
| WO | 2022056299 A1 | 3/2022 | |

OTHER PUBLICATIONS

An advanced human in vitro Co-culture model for translocation studies across the placental barrier Scientific Reports 8:5388 (2018)). (Year: 2018).*

Zeng, et al., "Developments of a Fully Automated Parallel HPLC/Mass Spectrometry System for the Analytical Characterization and Preparative Purification of Combinatorial Libraries", Analytical Chemistry, vol. 70, Issue 20, 1998, pp. 4380-4388.

Schettler, "Human Exposure to Phthalates via Consumer Products", International Journal of Andrology, vol. 29, 2006, pp. 134-139.

Schmidt, et al.,"Only Humans Have Human Placentas: Molecular Differences Between Mice and Humans", American Journal of Reproductive Immunology, vol. 108, Apr. 2015, pp. 65-71.

Shockcor, et al.,"Combined HPLC, NMR Spectroscopy, and Ion-Trap Mass Spectrometry with Application to the Detection and Characterization of Xenobiotic and Endogenous Metabolites in

(56) References Cited

OTHER PUBLICATIONS

Human Urine", Analytical Chemistry, vol. 68, Issue 24, 1996, pp. 4431-4435.
Sibley, et al., "Knowledge Needed About the Exchange Physiology of the Placenta", Placenta, vol. 64 Supplement 1, Apr. 2018, pp. S9-S15.
Takao, et al., "Isolation and Characterization of Human Trophoblast Side-Population (SP) Cells in Primary Villous Cytotrophoblasts and HTR-8/SVneo Cell Line", PLoS One, vol. 6, Issue 7, 2011, pp. e21990.
Tang, et al., "Pathway Confirmation and Flux Analysis of Central Metabolic Pathways in Desulfovibrio Vulgaris Hildenborough Using Gas Chromatography-Mass Spectrometry and Fourier Transform-Ion Cyclotron Resonance Mass Spectrometry", Journal of Bacteriology, vol. 189, No. 3, Feb. 2007, pp. 940-949.
Turco, et al., "Trophoblast Organoids as a Model for Maternal-fetal Interactions During Human Placentation", Nature, vol. 564, Issue 7735, Dec. 2018, pp. 263-267.
Van, et al., "Membrane Lipids: Where They Are and How They Behave", Nature Reviews Molecular Cell Biology, vol. 9, Feb. 2008, pp. 112-124.
Wishart, et al., "HMDB 4.0: The Human Metabolome Database for 2018", Nucleic Acids Research, vol. 46, Issue D1, Jan. 4, 2018, pp. D608-D617.
Zampieri, et al., "Frontiers of High-Throughput Metabolomics", Current Opinion in Chemical Biology, vol. 36, Feb. 2017, pp. 15-23.
Zan, et al., "AH Peptide-mediated Formation of Charged Planar Lipid Bilayers", The Journal of Physical Chemistry B, vol. 118, Issue 13, Apr. 3, 2014, pp. 3616-3621.
Zan, et al., "Rupture of Zwitterionic Lipid Vesicles by an Amphipathic, α-Helical Peptide: Indirect Effects of Sensor Surface and Implications for Experimental Analysis", Colloids and surfaces B: Biointerfaces, vol. 121, Sep. 2014, pp. 340-346.
"19th WHO Model List of Essential Medicines", 19th Edition, Apr. 2015, 53 pages.
"Control of the Leishmaniases: Report of a meeting of the WHO Expert Committee on the Control of Leishmaniases", WHO technical Report series—949, Mar. 22-26, 2010, 202 pages.
"Treating for Two: Medicine and Pregnancy", Centers for Disease Control and Prevention (CDC), Retreived form "https://www.cdc.gov/pregnancy/meds/treatingfortwo/index.html", 2020.
Abhishek, et al., "In Vitro Toxicity Evaluation of Low Doses of Pesticides in Individual and Mixed Condition on Human Keratinocyte Cell Line", Bioinformation, vol. 10, Issue 12, 2014, pp. 716-720.
Aengenheister, et al., "An Advanced Human in Vitro Coculture Model for Translocation Studies Across the Placental Barrier", Scientific Reports, vol. 8, Article No. 5388, Mar. 29, 2018, 12 pages.
Alberts, et al., "The Lipid Bilayer", Molecular Biology of the Cell. 4th edition. New York: Garland Science, 2002, 8 pages.
Ali, et al., "Preparation, Characterization and Transport of Dexamethasone—Loaded Polymeric Nanoparticles Across a Human Placental in Vitro Model", International Journal of Pharmaceutics, vol. 454, Issue 1, Sep. 15, 2013, pp. 149-157.
Baig, et al., "Lipidomic Analysis of Human Placental Syncytiotrophoblast Microvesicles in Adverse Pregnancy Outcomes", Placenta, vol. 34, Issue 5, May 2013, pp. 436-432.
Bailey, et al., "Effects of Flow and Bulk Vesicle Concentration on Supported Lipid Bilayer Formation", Langmuir, vol. 33, Issue 43, Oct. 21, 2017, pp. 11986-11997.
Barenholz, et al., "A Simple Method for the Preparation of Homogeneous Phospholipid Vesicles", Biochemistry, vol. 16, Issue 12, Jun. 14, 1977, pp. 2806-2810.
Belov, et al., "Zeptomole-Sensitivity Electrospray Ionization-Fourier Transform Ion Cyclotron Resonance Mass Spectrometry of Proteins", Analytical Chemistry, vol. 72, 2000, pp. 2271-2279.
Berben, et al., "Drug Permeability Profiling Using Cell-Free Permeation Tools: Overview and Applications", European Journal of Pharmaceutical Sciences, vol. 119, Jul. 1, 2018, pp. 219-233.
Bermejo, et al., "PAMPA—A Drug Absorption in Vitro Model 7. Comparing Rat in Situ, Caco-2, and PAMPA Permeability of Fluoroquinolones", European Journal of Pharmaceutical Sciences, vol. 21, Issue 4, Mar. 2004, pp. 429-441.
Bligh, et al., "A Rapid Method of Total Lipid Extraction and Purification", Canadian Journal of Biochemistry and Physiology, vol. 37, Issue 8, Aug. 1959, pp. 911-917.
Blundell, et al., "Placental Drug Transport-on-a-Chip: A Microengineered in Vitro Model of Transporter-Mediated Drug Efflux in the Human Placental Barrier", Advanced Healthcare Materials, vol. 7, Issue 2, Jan. 2018, pp. 1-9.
Bode, et al., "In Vitro Models for Studying Trophoblast Transcellular Transport", Methods in Molecular Medicine, vol. 122, 2006, pp. 225-239.
Brown, et al., "A Lipidomic Analysis of Placenta in Preeclampsia: Evidence for Lipid Storage", PLoS One, vol. 11 No. 9, Sep. 29, 2016, pp. e0163972.
Brown, et al., "Mass Spectrometry Tools and Metabolite-Specific Databases for Molecular Identification in Metabolomics", Analyst, vol. 134, Issue 7, Apr. 9, 2009, pp. 1322-1332.
Cao, et al., "Placental Microbiome and Its Role in Preterm Birth", NeoReviews, vol. 15, Issue 12, Dec. 2014, pp. e537-e545.
Cho, et al., "Alpha-helical Peptide-Induced Vesicle Rupture Revealing New Insight Into the Vesicle Fusion Process as Monitored in Situ by Quartz Crystal Microbalance—Dissipation and Reflectometry", Analytical Chemistry, vol. 81, Issue 12, Jun. 15, 2009, pp. 4752-4761.
Cho, et al., "Employing an Amphipathic Viral Peptide to Create a Lipid Bilayer on Au and TiO2", Journal of the American Chemical Society, vol. 129, Issue 33, Sep. 2007, pp. 10050-10051.
Cho, et al., "Mechanism of an Amphipathic Alpha-helical Peptide's Antiviral Activity Involves Size-dependent Virus Particle Lysis", ACS Chemical Biology, vol. 4, Issue 12, Dec. 18, 2009, pp. 1061-1067.
Czamara, et al., "Raman Spectroscopy of Lipids: A review", Journal of Raman Spectroscopy, vol. 46, Issue 1, Jan. 2015, 2 pages.
Dadelszen, et al., "Antihypertensive Medications in Management of Gestational Hypertension-Preeclampsia", Clinical Obstetrics and Gynecology, vol. 48, Issue 2, Jun. 2005, pp. 441-459.
Guttmacher, et al., "The Human Placenta Project: Placental Structure, Development, and Function in Real Time", Placenta, vol. 35, Issue 5, May 2014, pp. 303-304.
Hardy, et al., "Biomimetic Supported Lipid Bilayers With High Cholesterol Content Formed by α-Helical Peptide-Induced Vesicle Fusion", Journal of Materials Chemistry, vol. 22, Issue 37, Aug. 28, 2012, pp. 19506-19513.
Hardy, et al., "Model Cell Membranes: Techniques to Form Complex Biomimetic Supported Lipid Bilayers via Vesicle Usion", Current Opinion in Colloid & Interface Science, vol. 18, Issue 5, Oct. 1, 2013, pp. 448-458.
Richter, et al., "Following the Formation of Supported Lipid Bilayers on Mica: A Study Combining AFM, QCM-D, and Ellipsometry", Biophysical Journal, vol. 88, Issue 5, May 2005, pp. 3422-3433.
Hay, "Placental Transport of Nutrients to the Fetus", Hormone Research, vol. 42, Issue 4-5, 1994, pp. 215-222.
Huang, et al., "Increased Placental Phospholipid Levels in Pre-Eclamptic Pregnancies", International Journal of Molecular Sciences, vol. 14, Issue 2, 2013, pp. 3487-3499.
Pilmis, et al., "Extended-spectrum Beta-lactamase-producing Enterobacteriaceae (Esbl-pe) Infections: Are Carbapenem Alternatives Achievable in Daily Practice?", International Journal of Infectious Diseases, vol. 39, 2015, pp. 62-67.
Hubatsch, et al., "Determination of Drug Permeability and Prediction of Drug Absorption in Caco-2 Monolayers", Nature Protocols, vol. 2, Issue 9, 2007, pp. 2111-2119.
Jones, et al., "Regulation of Placental Nutrient Transport—A Review", Placenta, vol. 28, Issue 8-9, 2007, pp. 763-774.
Kaiser, "Reproductive Biology. Gearing Up for a Closer Look at the Human Placenta", Science, vol. 344, Issue 6188, Jun. 6, 2014, pp. 1073.
Kalkunte, et al., "In Vitro and In Vivo Evidence for Lack of Endovascular Remodeling by Third Trimester Trophoblasts", Placenta, vol. 29, Oct. 2008, pp. 871-878.

(56) References Cited

OTHER PUBLICATIONS

Kaminski, et al.,"Recent Progress in the Study of the Interactions of Amphotericin B with Cholesterol and Ergosterol in Lipid Environments", European Biophysics Journal , vol. 43, Issue 10-11, 2014, pp. 453-467.
Karger,"HPLC: Early and Recent Perspectives", Journal of Chemical Education, vol. 74, Issue 1, 1997, pp. 45.
Keller, et al.,"Surface Specific Kinetics of Lipid Vesicle Adsorption Measured with a Quartz Crystal Microbalance", Biophysical Journal, vol. 75, Issue 3, 1998, pp. 1397-1402.
Knofler,"Critical Growth Factors and Signalling Pathways Controlling Human Trophoblast Invasion", The International Journal of Developmental Biology, vol. 54, Issue 2-3, 2010, pp. 269-280.
Korkes, et al.,"Lipidomic Assessment of Plasma and Placenta of Women with Early-Onset Preeclampsia", PLoS One, vol. 9, Issue 10, 2014, 9 pages.
Lee, et al.,"Placenta-on-a-Chip: A Novel Platform to Study the Biology of the Human Placenta", Journal of Maternal—Fetal and Neonatal Medicine, vol. 29, Issue 7, 2016, pp. 1046-1054.
Lewis, et al.,"Partial Characterization of an Immortalized Human Trophoblast Cell-Line, TCL-1, which Possesses a CSF-1 Autocrine Loop", Placenta, vol. 17, 1996, pp. 136-146.
Masungi, et al.,"Parallel Artificial Membrane Permeability Assay (PAMPA) Combined with a 10-Day Multiscreen Caco-2 Cell Culture as a Tool for Assessing New Drug Candidates", Pharmazie, vol. 63 , Issue 3, 2008, pp. 194-199.
Messerlian, et al.,"Urinary Concentrations of Phthalate Metabolites in Relation to Pregnancy Loss among Women Conceiving with Medically Assisted Reproduction", Epidemiology, vol. 27, Issue 6, Nov. 2016, pp. 879-888.
Muoth, et al.,"A 3D Co-Culture Microtissue Model of the Human Placenta for Nanotoxicity Assessment", Nanoscale, vol. 8, Issue 39, 2016, pp. 17322-17332.
Orendi, et al.,"Placental and Trophoblastic in Vitro Models to Study Preventive and Therapeutic Agents for Preeclampsia", Placenta, vol. 32 Supplement 1, Feb. 2011, pp. S49-S54.
Orendi, et al.,"The Choriocarcinoma Cell Line Bewo: Syncytial Fusion and Expression of Syncytium-specific Proteins", Reproduction, vol. 140, 2010, pp. 759-766.
Paglia, et al.,"The Use of Oral Antidiabetic Medications in Gestational Diabetes Mellitus", Current Diabetes Reports, vol. 9, Issue 4, Aug. 2009, pp. 287-290.
Pasca, et al.,"The Placenta: The Lost Neuroendocrine Organ", NeoReviews, vol. 11, No. 2, Feb. 2010, pp. e64-e77.
Piazza, et al.,"Environmental Toxins and the Impact of Other Endocrine Disrupting Chemicals in Women's Reproductive Health", JBRA Assisted Reproduction, vol. 23, Issue 2, 2019, pp. 154-164.
Pichler, et al.,"Modification of Membrane Lipid Compositions in Single-Celled Organisms—From Basics to Applications", Methods, vol. 147, Sep. 1, 2018, pp. 50-65.
Pilmis, et al.,"Antifungal Drugs During Pregnancy: An Updated Review", Journal of Antimicrobial Chemotherapy, vol. 70, Issue 1, 2015, pp. 14-22.
Graham, et al., "Establishment and Characterization of First Trimester Human Trophoblast Cells with Extended Life-Span", Experimental Cell Research, vol. 206, 1993, pp. 204-211.
"Antibiotic / Antimicrobial Resistance (AR / AMR)", (2017, Sep. 19). Retrieved Jan. 15, 2018, from https://www.cdc.gov/drugresistance/about.html., 3 pages.
"Antibiotic Resistance Threats in the United States", U.S. Department Health & Human Services, Center for Disease Control and Prevention, 2013, 114 pages.
"Identification of Candida auris", Retrieved on Apr. 11, 2024 from https://www.cdc.gov/fungal/candida-auris/identification.html, 6 pages.
"International Search Report and Written Opinion received for PCT Patent Application No. PCTUS2019041884, mailed on Nov. 15, 2019", 11 pages.
"International Search Report and Written Opinion received for PCT Patent Application No. PCT/US2020/057799, dated Jan. 29, 2021", 8 pages.
Alexander , et al., "Increasing Echinocandin Resistance in Candida G/Abrata: Clinical Failure Correlates With Presence of FKS Mutations and Elevated Minimum Inhibitory Concentrations", Clinical Infectious Diseases, vol. 56, No. 12, Jun. 2013, pp. 1724-1732.
Alkekhia, et al., "β-Lactamase-Responsive Hydrogel Drug Delivery Platform for Bacteria-Triggered Cargo Release", CS Applied Materials & Interfaces, vol. 14, No. 24, Jun. 8, 2022, pp. 27538-27550.
Almeida , et al., "Recent Progress in Bioconjugation Strategies for Liposome-Mediated Drug Delivery", Molecules, vol. 25, 2020, p. 5672.
Ambati , et al., "Dectin-1-targeted antifungal liposomes exhibit enhanced efficacy", mSphere, vol. 4, No. 1, e00025-19, Jan./Feb. 2019, 15 pages.
Ambati , et al., "Dectin-2-Targeted Antifungal Liposomes Exhibit Enhanced Efficacy", mSphere, vol. 4, 2019, pp. e00715-e00719.
Ashley , et al., "Hydrogel Drug Delivery System With Predictable and Tunable Drug Release and Degradation Rates", PNAS, vol. Vol. 110, No. 6, Feb. 5, 2013, pp. 2318-2323.
Atta, et al., "Solution-Based Ultra-Sensitive Surface-Enhanced Raman Scattering Detection of the Toxin Bacterial Biomarker Pyocyanin in Biological Fluids Using Sharp-Branched Gold Nanostars", Analytical chemistry, vol. 95, Jan. 24, 2023, pp. 2690-2697.
Avrahami , et al., "A New Group of Antifungal and Antibacterial Lipopeptides Derived from Non-membrane Active Peptides Conjugated to Palmitic Acid", The Journal of Biological Chemistry, vol. 279, Issue 13, Jan. 6, 2004, pp. 12277-12285.
Azzopardi , et al., "The enhanced permeability retention effect: a new paradigm for drug targeting in infection", J Antimicrob Chemother., vol. 68, 2013, pp. 257-274.
Baddley , et al., "Association of Fluconazole Pharmacodynamics With Mortality in Patients With Candidemia", Antimicrobial Agents and Chemotherapy, vol. 52, No. 9, Sep. 2008, pp. 3022-3028.
Bae , et al., "Injectable Biodegradable Hydrogels: Progress and Challenges", Journal of Materials Chemistry B, vol. 1, 2013, pp. 5371-5388.
Bahney , et al., "Visible Light Photoinitiation of Mesenchymal Stem Cell-Laden Bioresponsive Hydrogels", European Cells & Materials, vol. 22, 2011, 24 pages.
Bapat , et al., "Photodynamic Therapy is Effective Against Candida auris Biofilms", Frontiers in Cellular and Infection Microbiology, vol. 11, Article 713092, Sep. 2021, 15 pages.
Barret, David , "From Natural Products to Clinically Useful Antifungals", Biochimica et Biophysica Acta, vol. 1587, 2002, pp. 224-233.
Bebrone , et al., "CENTA as a Chromogenic Substrate for Studying beta-Lactamases", Antimicrobial Agents and Chemotherapy. vol. 45, No. 6, 2001, pp. 1868-1871.
Bernabeau , et al., "Evaluation of the Beta-CARBA test, a colorimentric test for the rapid detection of carbapenemase activity in Gram-negative bacilli", Journal of Antimicrobial Chemotherapy, vol. 72, No. 6, Jun. 2017, pp. 1646-1658.
Boccalini , et al., "Methylene Blue-Containing Liposomes as New Photodynamic Anti-Bacterial Agents", Journal of Material Chemistry, vol. 5, 2017, pp. 2788-2797.
Bodelon , et al., "Surface-Enhanced Raman Scattering Spectroscopy for Label-Free Analysis of P. aeruginosa Quorum Sensing", Frontiers in Cellular and Infection Microbiology, vol. 8, Article 143, May 2018, 17 pages.
Borelli , et al., "X-ray Structures of Sap1 and Sap5: Structural Comparison of the Secreted Aspartic Proteinases From Candida Albicans", Proteins: Structure, Function, and Bioinformatics, vol. 72, 2008, pp. 1308-1319.
Braga , et al., "Screening of Yeasts From Brazilian Amazon Rain Forest for Extracellular Proteinases Production", Systematic and Applied Microbiology, vol. 21, 1998, pp. 353-359.
Brown, Gordon D., "Dectin-1: a signalling non-TLR pattern-recognition receptor", Nat Rev Immunol., vol. 6, 2006, pp. 33-43.
Brown , et al., "Structure of the Fungal B-glucan-binding Immune Receptor Dectin-1: Implications for Function", Protein Science, vol. 16, 2007, pp. 1042-1052.
Casadevall , et al., "On the Emergence of Candida auris: Climate Change, Azoles, Swamps, and Birds", mBio, vol. 10, Issue 4, 2019, 7 pages.

(56) References Cited

OTHER PUBLICATIONS

Chan, et al., "Unique Fluorescent Imaging Probe for Bacterial Surface Localization and Resistant Enzyme Imaging", ACS Chemical Biology, vol. 13, 2018, pp. 1890-1896.

Chou, et al., "Characterization of Photocrosslinked Alginate Hydrogels for Nucleus Pulposus Cell Encapsulation", J Biomed Mater Res A, vol. 91, Sep. 11, 2008, pp. 187-194.

Ciloglu, "Drug-Resistant *Staphylococcus aureus* Bacteria Detection by Combining Surface-Enhanced Raman Spectroscopy (SERS) and Deep Learning Techniques", Scientific Reports, vol. 11, No. 18444, 2021, 12 pages.

Coin, et al., "Solid-Phase Peptide Synthesis: From Standard Procedures to the Synthesis of Difficult Sequences", Nature Protocols, vol. 2, No. 12, 2007, pp. 3247-3256.

Costa, et al., "Freeze-Anneal-Thaw Cycling of Unilamellar Liposomes: Effect on Encapsulation Efficiency", Pharmaceutical Research, vol. 31, 2014, pp. 97-103.

Danese, Paul N., "Antibiofilm Approaches: Prevention of Catheter Colonization", Chemistry & Biology, vol. 9, Aug. 2002, pp. 873-880.

Dehghani, et al., "14.3.6—Injectable Hydrogels for in Vivo Cartilage Formation", Chapter—Challenges for Cartilage Regeneration, Biomaterials for Implants and Scaffolds, 2016, p. 422.

Díez-Martínez, et al., "Auranofin-Loaded Nanoparticles as a New Therapeutic Tool to Fight Streptococcal Infections", Scientific Reports, vol. 6, Jan. 18, 2016, pp. 1-12.

Drawz, et al., "Three Decades of β-Lactamase Inhibitors", Clinical Microbiology Reviews, vol. 23, No. 1, 2010, pp. 160-201.

Drummond, et al., "The Role of Dectin-1 in the Host Defence Against Fungal Infections", Current Opinion in Microbiology, vol. 14, 2011, pp. 392-399.

Durst, et al., "Flexural Characterization of Cell Encapsulated PEGDA Hydrogels With Applications for Tissue Engineered Heart Valves", Acta Biomaterialia, vol. 7, No. 6, Jun. 2011, 22 pages.

Eggimann, et al., "Epidemiology of *Candida* Species Infections in Critically Ill Non-Immunosuppressed Patients", Lancet Infect Dis., vol. 3, No. 11, Nov. 2003, pp. 685-702.

Fang, et al., "Robust Self-Healing Hydrogels Assisted by Cross-Linked Nanofiber Networks", Scientific Reports, vol. 3, No. 2811, Oct. 3, 2013, pp. 1-7.

Federman, et al., "Targeting Liposomes Toward Novel Pediatric Anticancer Therapeutics", Pediatric Research, vol. 67, No. 5, 2010, pp. 514-519.

Filgueiras, "Adsorption Study of Antibiotics on Silver Nanoparticle Surfaces by Surface-Enhanced Raman Scattering Spectroscopy", Spectrochimica Acta Part A: Molecular and Biomolecular Spectroscopy, vol. 136, Part B, Feb. 5, 2015, pp. 979-985.

Franco, et al., "Development and Optimization of a Dual-Photoinitiator, Emulsion-Based Technique for Rapid Generation of Cell-Laden Hydrogel Microspheres", Acta Biomaterialia, vol. 7, No. 9, 2011, pp. 3267-3276.

Franssen, et al., "A Novel Preparation Method for Polymeric Microparticles Without the Use of Organic Solvents", International Journal of Pharmaceutics, vol. 168, No. 1, 1998, 1 page.

Fuchs, et al., "Inhibition of Bacterial and Fungal Pathogens by the Orphaned Drug Auranofin", Future Medicinal Chemistry, vol. 8, Issue 2, 2016, pp. 117-132.

Fusek, et al., "Extracellular Aspartic Proteinases From Candida Albicans, Candida Tropicalis, and Candida Parapsilosis Yeasts Differ Substantially in Their Specificities", Biochemistry, vol. 33, 1994, pp. 9791-9799.

Gabriella, et al., "Efficacy of a Central Venous Catheter (Hydrocath®) Loaded with Teicoplanin in Preventing Subcutaneous Staphylococcal Infection in the Mouse", Zentralblatt Fur Bakteriol, vol. 279, 1993, pp. 426-433.

Galvan, et al., "Surface-Enhanced Raman Scattering for Rapid Detection and Characterization of Antibiotic-Resistant Bacteria", Advanced Healthcare Materials, vol. 7, Issue 13, 2018, pp. 1-27.

Germaine, et al., "Proteolytic Activity of Candida Albicans: Action on Human Salivary Proteins", Infection and Immunity, vol. 22, No. 3, Dec. 1978, pp. 861-866.

Page, et al., "Mechanism of β-lactam Ring Opening in Cephalosporins", Journal of the American Chemical Society, vol. 106, 1984, pp. 3820-3825.

Gong, et al., "Translocation of cell-penetrating peptidesintoCandidafungal pathogens", Protein Science. vol. 26, No. 9, 2017, pp. 1687-1892.

Gow, et al., "Candida Albicans Morphogenesis and Host Defence: Discriminating Invasion From Colonization", Nat Rev Microbiol. vol. 10, No. 2, 2012, pp. 112-122.

Grubb, et al., "Candida albicans—Endothelial Cell Interactions: a Key Step in the Pathogenesis of Systemic Candidiasis", Infection and Immunity, vol. 76, No. 10, Oct. 2008, pp. 4370-4377.

Hamley, Ian W, "Lipopeptides: From Self-assembly to Bioactivity", Chemical Communications—Royal Society of Chemistry, vol. 51, 2015, pp. 8574-8583.

Hanaki, et al., "Characterization of HMRZ-86: a novel chromogenic cephalosporin for the detection of extended-spectrum beta-lacatamases,", Journal of Antimicrobial Chemotherapy, vol. 53, No. 5, May 2004, pp. 888-889.

Hanaki, et al., "The Synthesis of 7-Substituted-3-dinitrostyryl Cephalosporins and Their Ability for Detecting Extended Spectrum Beta-Lactamases (ESBLs).", The Journal of Antibiotics, vol. 58, 2005, pp. 69-73.

Harbut, et al., "Auranofin Exerts Broad-spectrum Bactericidal Activities by Targeting Thiol-redox Homeostasis", Proceedings of the National Academy of Sciences, U S A., vol. 112, Issue 14, Apr. 7, 2015, pp. 4453-4458.

Hashimoto, et al., "Micafungin: A Sulfated Echinocandin", The Journal of Antibiotics, vol. 62, Issue 1, 2009, pp. 27-35.

Hassanain, et al., "Recent Advances in Antibiotic Resistance Diagnosis Using SERS: Focus on the "Big 5" Challenges", The Royal Society of Chemistry, vol. 147, Sep. 13, 2022, pp. 4674-4700.

Hilton, et al., "Phenotypically Distinguishing ESBL-Producing Pathogens Using Paper-Based Surface Enhanced Raman Sensors", Analytica Chimica Acta, vol. 1127, Aug. 29, 2020, pp. 207-216.

Hoffman, Paul S., "Antibacterial Discovery: 21st Century Challenges", Antibiotics, vol. 9, No. 5, 2020, 10 pages.

Horn, et al., "Epidemiology and Outcomes of Candidemia in 2019 Patients: Data From the Prospective Antifungal Therapy Alliance Registry", Clinical Infectious Diseases, vol. 48, No. 12, Jun. 15, 2009, pp. 1695-1703.

Hsu, et al., "Prognostic Factors for Patients With Culture-Positive Candida Infection Undergoing Abdominal Surgery", J. Microbial. Immunol. Infect., vol. 42, No. 5, Oct. 2009, 1 page.

Hube, et al., "Expression of Seven Members of the Gene Family Encoding Secretory Aspartyl Proteinases in Candida Albicans", Molecular Microbiology, vol. 14, No. 1, 1994, 1 page.

Jang, Woong Sik, et al., "The P-113 Fragment of Histatin 5 Requires a Specific Peptide Sequence for Intracellular Translocation in Candida albicans, which is Independent of Cell Wall Binding", Antimicrobial Agents and Chemotherapy, vol. 52, No. 2, Feb. 2008, pp. 497-504.

Jarvis, et al., "Predominant Pathogens in Hospital Infections", J Antimicrob Chemother., vol. 29, Apr. 1992, 1 page.

Jiang, et al., "Clearance of Intracellular Klebsiella Pneumoniae Infection Using Gentamicinloaded Nanoparticles", Journal of Controlled Release, vol. 279, 2018, pp. 316-325.

Jones, et al., "In vitro evaluation of CENTA, a new beta-lactamase-susceptible chromogenic cephalosporin reagent.", Journal of Clinical Microbiology, vol. 15, No. 5, 2015, pp. 954-958.

Kabir, et al., "Candida albicans: A Model Organism for Studying Fungal Pathogens", International Scholarly Research Network, vol. 2012, Article ID 538694, 2012, pp. 1-15.

Kargar Dong-Jin, et al., "Application Potential of Liposomal Delivery Systems Prepared by Lipids Extracted from *E. coli* Cultures", Annual Research & Review in Biology, vol. 4, No. 8, Jan. 2014, pp. 1319-1329.

Kendrick, et al., "Online Size-Exclusion High-Performance Liquid Chromatography Light Scattering and Differential Refractometry Methods to Determine Degree of Polymer Conjugation to Proteins

(56) References Cited

OTHER PUBLICATIONS and Protein-Protein or Protein-Ligand Association States", Analytical Biochemistry, vol. 299, No. 2, 2001, pp. 136-146.

Khan, et al., "Rapid optical determination of β-lactamase and antibiotic activity", BMC Microbiol., vol. 14, 2014, 14 pages.

Khetan, et al., "Degradation-mediated Cellular Traction Directs Stem Cell Fate in Covalently Crosslinked Three-dimensional hydrogels", Nat Mater, vol. 12, No. 5, May 2013, pp. 458-465.

Khetan, et al., "Sequential Crosslinking to Control Cellular Spreading in 3-dimensional Hydrogels", Soft Matter, vol. 5, 2009, pp. 1601-1606.

Kim, et al., "Engineering Peptide-targeted Liposomal Nanoparticles Optimized for Improved Selectivity for HER2-positive Breast Cancer Cells to Achieve Enhanced in Vivo Efficacy", Journal of Controlled Release, vol. 322, 2020, pp. 530-541.

Kischkel, et al., "Therapies and Vaccines Based on Nanoparticles for the Treatment of Systemic Fungal Infections", Front Cell Infect Microbiol., vol. 10, 2020, 25 pages.

Korobova, et al., "The Application of Selective Chromogenic Agar for Detecting Enterobacteria with Production of Beta-Lactamases", Klin Lab Diagn, vol. 60, No. 11, 2015, pp. 53-57.

Koutsopoulos, et al., "Controlled Release of Functional Proteins Through Designer Self-Assembling Peptide Nanofiber Hydrogel Scaffold", Proceedings of the National Academy of Sciences, vol. 106, No. 12, Mar. 24, 2009, pp. 4623-4628.

Lamastro, et al., "Antifungal Liposomes: Lipid Saturation and Cholesterol Concentration Impact Interaction With Fungal and Mammalian Cells", Journal of Biomedical Materials Research Part A, vol. 111, 2023, pp. 644-659.

Lee, et al., "Antifungal Drug Resistance: Molecular Mechanisms in Candida albicans and Beyond", Chem Rev., vol. 121, 2021, pp. 3390-3411.

Li, et al., "Enzyme-Responsive Polymeric Vesicles for Bacterial-Strain-Selective Delivery of Antimicrobial Agents", Angewandte Chemie International Edition, vol. 55, No. 5, 2016, pp. 1760-1764.

Li, et al., "Using Galleria Mellonella-Candida Albicans Infection Model to Evaluate Antifungal Agents", Biological and Pharmaceutical Bulletin, vol. 36, No. 9, 2013, pp. 1482-1487.

Liang, et al., "Functional Hydrogels as Wound Dressing to Enhance Wound Healing", ACS Nano, vol. 15, 2021, pp. 12687-12722.

Lim Dong-Jin, "Methylene Blue-Based Nano and Microparticles: Fabrication and Applications in Photodynamic Therapy", Polymers, vol. 13, No. 22, Article No. 3955, Nov. 16, 2021, pp. 1-15.

Liu, et al., "Auranofin Releasing Antibacterial and Antibiofilm Polyurethane Intravascular Catheter Coatings", Frontier in Cellular and Infection Microbiology, vol. 9, No. 37, Feb. 28, 2019, pp. 1-13.

Livermore, et al., "Evaluation of the chromogenic Cia-Beta-Test for detecing extended-spectrum, AmpC and metallo-Beta-lactamases", Journal of Antimicrobial Chemotherapy, vol. 60, No. 6,, 2007, pp. 1375-1379.

Lockhart, et al., "Simultaneous Emergence of Multidrug-Resistant Candida Auris on 3 Continents Confirmed by Whole-Genome Sequencing and Epidemiological Analyses", Clinical Infectious Diseases : An Official Publication of the Infectious Diseases Society of America, vol. 64, 2017, pp. 134-140.

Lockhart, et al., "Species Identification and Antifungal Susceptibility Testing of Candida Bloodstream Isolates From Population-Based Surveillance Studies in Two U.S. Cities from 2008 to 2011", J Clin Microbiol., vol. 50, No. 11, Nov. 2012, pp. 3435-3442.

Magill, et al., "Multistate Point-Prevalence Survey of Health Care-Associated Infections", The New England Journal of Medicine, vol. 370, No. 13, 2014, pp. 1198-1208.

Majcher, et al., "Hydrogel Synthesis and Design", in Functional Biopolymers, Polymers and Polymeric Composites: A Reference Series, 2018, 41 pages.

Maki, et al., "The Risk of Bloodstream Infection in Adults with Different Intravascular Devices: A Systematic Review of 200 Published Prospective Studies", Mayo Clinic Proceedings, vol. 81, No. 9, Sep. 2006, pp. 1159-1171.

Melchels, et al., "5.542.3.3.2.—Printing Cell-laden 3d Hydrogel Constructs", Chapter—5.542—Organ Printing, Comprehensive Biomaterials, vol. 5, 2011, p. 601.

Mishra, et al., "Pathogenicity and Drug Resistance in Candida Albicans and Other Yeast Species—A Review", Acta Microbiol Immunol Hung, vol. 54, No. 3, Sep. 2007, pp. 201-235.

Moore, et al., "AmBisome: Liposomal Formulation, Structure, Mechanism of Action and Pre-clinical Experience", Journal of Antimicrobial Chemotherapy, vol. 49, Suppl 1, Feb. 2002, pp. 21-30.

Morandi, et al., "Nanomolar inhibitors of AmpC Beta-lactamase", J. Am. Chem. Soc., vol. 125, 2003, pp. 685-695.

Morgan, et al., "Excess Mortality, Hospital Stay, and Cost Due to Candidemia: a Case-control Study Using Data From Population-based Candidemia Surveillance", Infection Control and Hospital Epidemiology, vol. 26, No. 6, Jun. 2005, pp. 540-547.

Mura, et al., "Development of a novel chromogenic method, Penta-well test, for rapid predictoin of Beta-lactamase classes provuded in clinical Enterobacteriaceae isolates.", Diagnostic Microbiology and Infectious Disease, vol. 83, 2015, pp. 25-29.

Odds, et al., "Antifungal Agents: Mechanisms of Action", Trends Microbiology, vol. 11, Issue 6, Jun. 2003, pp. 272-279.

Park, Seong-Cheol, et al., "Targeting and Synergistic Action of an Antifungal Peptide in an Antibiotic Drug-Delivery System", Journal of Controlled Release, vol. 256, 2017, pp. 46-55.

Zhou, et al., "In Vivo Anti-Biofilm and Anti-Bacterial Non-Leachable Coating Thermally Polymerized on Cylindrical Catheter", ACS Applied Materials and Interfaces, vol. 9, 2017, pp. 36269-36280.

Perlin, David S, "Echinocandin Resistance in Candida", CID, vol. 61, Suppl. 6, 2015, pp. S612-S617.

Pfaller, et al., "Epidemiology of Invasive Candidiasis: A Persistent Public Health Problem", Clinical Microbiology Reviews, vol. 20, No. 1, Jan. 2007, pp. 133-163.

Pivetta Dong-Jin, et al., "Liposomes Encapsulating Methylene Blue and Acridine Orange: An Approach for Phototherapy of Skin Cancer", Colloids and Surfaces B: Biointerfaces, vol. 220, No. 112901, Dec. 2022, 7 pages.

Plou, et al., "Nanocomposite Scaffolds for Monitoring of Drug Diffusion in Three-Dimensional Cell Environments by Surface-Enhanced Raman Spectroscopy", Nano Letters, vol. 21, Oct. 6, 2021, pp. 8785-8793.

Rappsilber, et al., "Stop and Go Extraction Tips for Matrix-Assisted Laser Desorption/Ionization, Nanoelectrospray, and LC/MS Sample Pretreatment in Proteomics", Analytical Chemistry, vol. 75, No. 3, 2003, 1 page.

Richards, et al., "Nosocomial infections in coronary care units in the United States", The America Journal of Cardiology, vol. 82, Sep. 15, 1998, pp. 789-793.

Richardson, et al., "Special Issue: Mucosal Fungal Infections", Journal of Fungi, vol. 4, Issue 43, 2018, pp. 1-3.

Roemer, et al., "Antifungal Drug Development: Challenges, Unmet Clinical Needs, and New Approaches", Cold Spring Harbor Perspectives in Medicine, vol. 4, Issue a019703, 2014, pp. 1-14.

Rothstein, et al., "Anticandida Activity is Retained in P-113, A 12-Amino-Acid Fragment of Histatin 5", Antimicrobial Agents and Chemotherapy, vol. 45, No. 5, 2001, pp. 1367-1373.

Samek, et al., "The Potential of SERS as an AST Methodology in Clinical Settings", Nanophotonics, vol. 10, No. 10, Jul. 5, 2021, pp. 2537-2561.

Satoh, et al., "*Candida auris* Sp. Nov., a Novel Ascomycetous Yeast Isolated From the External Ear Canal of an Inpatient in a Japanese Hospital", Microbial Immunol, vol. 53, 2009, pp. 41-44.

Schaller, et al., "Hydrolytic Enzymes as Virulence Factors of Candida Albicans", Mycoses, vol. 48, 2005, pp. 365-377.

Schneider, et al., "Influence of Ph on Wound-healing: a New Perspective for Wound-therapy?", Arch Dermatol Res, vol. 298, 2007, pp. 413-420.

Schreiber, et al., "Proteolytic Activity of Candida Albicans and Other Yeasts", Diagnostic Microbiology and Infectious Disease, vol. 3, No. 1, 1985, 1 page.

Sercombe, et al., "Advances and Challenges of Liposome Assisted Drug Delivery", Front Pharmacol., vol. 6, 2015, 13 pages.

(56) References Cited

OTHER PUBLICATIONS

Shaikh, et al., "Antibiotic resistance and extended spectrum beta-lactamases: Types, epidemiology and treatment.", Saudi Journal of Biological Sciences, vol. 22, 2015, pp. 90-101.
Shao, et al., "Enzyme responsive luminescent ruthenium(II) cephalosporin probe for intracellular imaging and photoinactivation of antibiotics resistant bacteria", Chemical Communications, vol. 48, 2012, pp. 1739-1741.
Sharma, et al., "Drug Discovery of Antimicrobial Photosensitizers Using Animal Models", Current Pharmaceutical Design, vol. 17, No. 13, 2011, pp. 1303-1319.
Simner, et al., "Carbapenesmase Detection among Carbapenem-Resistant Glucose-Nonfermenting Gram-Negative Bacilli", J Clin Microbiol., vol. 55, 2017, pp. 2858-2864.
Souza, et al., "Distal and Lateral Toenail Onychomycosis Caused by Trichophyton rubrum: Treatment with Photodynamic Therapy Based on Methylene Blue Dye", Anais Brasileiros de Dermatologia, vol. 89, No. 1, 2014, pp. 184-186.
Stacey, Kevin, "Germ-Fighting Catheter Coating May Help Prevent Infections", News from Brown Available at <https://news.brown.edu/articles/2019/03/coating>, Mar. 7, 2019, 3 pages.
Stair, et al., "Sensor Materials for the Detection of Proteases", Biosensors and Bioelectronics, vol. 24, No. 7, 2009, 1 page.
Štefánek, et al., "Photodynamic Inactivation Effectively Eradicates Candida auris Biofilm despite Its Interference with the Upregulation of CDR1 and MDR1 Efflux Genes", Journal of Fungi, vol. 8, No. 1137, Oct. 27, 2022, pp. 1-10.
Tooke, et al., "Beta-Lactamases and Beta-Lactamase Inhibitors in the 21st Century", J Mol Biol., vol. 431, 2019, pp. 3472-3500.
Tsai, et al., "Galleria Mellonella Infection Models for the Study of Bacterial Diseases and for Antimicrobial Drug Testing", Virulence, vol. 7, Issue 3, Apr. 2016, pp. 214-229.
Vallabhaneni, et al., "Epidemiology and Risk Factors for Echinocandin Nonsusceptible Candida Glabrata Bloodstream Infections: Data From a Large Multisite Population-Based Candidemia Surveillance Program", Open Forum Infectious Diseases, vol. 2, No. 4, 2015, pp. 1-7.
Vallabhaneni, et al., "Investigation of the First Seven Reported Cases of Candida Auris, A Globally Emerging Invasive, Multidrug-Resistant Fungus-Fungus", American Journal of Transplantation, vol. 17, 2017, pp. 296-299.
Van Berkel, et al., "Assay platform for clinically relevant metallo-β-lactamases,", J. Med. Chem., vol. 56, 2013, pp. 6945-6953.
Vazquez, et al., "Anidulafungin: A Novel Echinocandin", Reviews of Anti-infective Agents, CID, vol. 43, Issue 215, Jul. 15, 2006, pp. 215-222.
Ventola, C Lee, "The Antibiotic Resistance Crisis: Part 1: Causes and Threats", Pharmacy and Therapeutics, vol. 40, No. 4, 2015, pp. 277-283.
Vrioni, et al., "Performal of the Beta LACTA test for rapid detection of expanded-spectrum cephalosporin-non-susceptible Enterobacteriaceae.", Journal of Global Antimicrobial Resistance, vol. 10,, 2017, pp. 285-288.
Waglewska, et al., "Antimicrobial Phyto-Photodynamic Activity Inducing by Polyphenol-Supported Methylene Blue Co-Loaded into Multifunctional Bilosomes: Advanced Hybrid Nanoplatform in the Skin Infections Treatment?", Journal of Photochemistry and Photobiology B: Biology, vol. 240, No. 112650, Mar. 2023, 7 pages.
Walker, et al., "The Viscoelastic Properties of the Fungal Cell Wall Allow Traffic of AmBisome as Intact Liposome Vesicles", American Society For Microbiology, vol. 9, Issue 1, Jan./Feb. 2018, 15 pages.
Wang, et al., "Detection and Characterization of Antibiotic-Resistant Bacteria Using Surface-Enhanced Raman Spectroscopy", Nanomaterials, vol. 8, No. 762, Sep. 26, 2018, pp. 1-21.
Wang, et al., "Plasmonic Microneedle Arrays for Rapid Extraction, SERS Detection, and Inactivation of Bacteria", Chemical Engineering Journal, vol. 442, Part 1, Article 136140, Aug. 15, 2022, 8 pages.
Wassef, et al., "Chromgenic Cica-Beta Testing for Detection of Extended-Spectrum and AmpC Beta-Lactamases Among Cefoxitin-Resistant Isolates", Laboratory Medicine, vol. 44, No. 1,, 2013, pp. 25-28.
Wu Dong-Jin, et al., "Methylene-Blue-Encapsulated Liposomes as Photodynamic Therapy Nano Agents for Breast Cancer Cells", Nanomaterials, vol. 9, No. 14, 2019, pp. 1-12.
Xiao, et al., "Novel Fluorescent Cephalosporins: Synthesis, Antimicrobial Activity and Photodynamic Inactivation of Antibiotic Resistant Bacteria", European Journal of Medicinal Chemistry, vol. 59, 2013, pp. 150-159.
Xin, et al., "Identification of a Monoacid-Based, Cell Permeable, Selective Inhibitor of Protein Tyrosine Phosphatase 1B", Bioorganic and Medicinal Chemistry Letters. vol. 13, 2003, pp. 3947-3950.
Xu, et al., "Bioorthogonally Cross-Linked Hydrogel Network with Precisely Controlled Disintegration Time over a Broad Range", J. Am. Chem. Soc, vol. 136, 2014, pp. 4105-4108.
Xu, et al., "Photoactive Silver Nanoagents for Backgroundless Monitoring and Precision Killing of Multidrug-Resistant Bacteria", Nanotheranostics, vol. 5, No. 4, Jun. 1, 2021, pp. 472-487.
Yang, et al., "Using β-Lactamase to Trigger Supramolecular Hydrogelation", Journal of the American Chemical Society, vol. 129, No. 2, 2007, pp. 266-267.
Yu, et al., "A chromogenic cephalosporin for Beta-lactamese inhibitor screening assays", Analytical Biochemistry, vol. 428, No. 2, 2012, pp. 96-98.
Yu, et al., "Site-Specific Photoconjugation of Beta-Lactamase Fragments to Monoclonal Antibodies Enables sensitive Analyte Deteciton via Split-Enzyme Complementation", Biotechnology Journal, vol. 13, 2018, 9 pages.
Yu, et al., "β-Lactamase Responsive Supramolecular Hydrogels with Host-Guest Self-Healing Capability", ACS Applied Polymer Materials,, 2019, pp. 55-65.
Zaidi, et al., "Total Protein Profile and Drug Resistance in Candida Albicans Isolated From Clinical Samples", Molecular Biology International, Article ID 4982131, 2016, 8 pages.
Zheng, et al., "Exploiting a Bacterial Drug-Resistance Mechanism: A Light-Activated Construct for the Destruction of MRSA", Angewandte Chemie International Edition, vol. 48, 2009, pp. 2148-2151.

* cited by examiner

Frequency and dissipation changes occurring due to DEHP interaction with bilayers

QCM-D plots with amphotericin B interactions

Cell % permeated and cell % interacting with bilayer using a parallel artificial permeability assay

PLACENTAL LIPID BILAYER FOR CELL-FREE MOLECULAR INTERACTION STUDIES

REFERENCE TO RELATED APPLICATIONS

This patent application claims priority under 35 U.S.C. § 119(e) to provisional patent applications U.S. Ser. No. 62/850,188, filed May 20, 2019; U.S. Ser. No. 62/905,756, filed Sep. 25, 2019; and U.S. Ser. No. 62/976,882, filed Feb. 14, 2020, all entitled "Placental Lipid Bilayer for Cell-Free Molecular Interaction Studies."

STATEMENT REGARDING FEDERALLY SPONSORED RESEARCH OR DEVELOPMENT

This invention was made with government support under Grant No. 1644760 awarded by the National Science Foundation (NSF). The government has certain rights in the invention.

FIELD OF THE INVENTION

This invention generally relates to heterogeneous membranes, e.g., containing dispersed material or mixed matrix membranes with "carriers" containing embedded or bound biomolecules.

BACKGROUND OF THE INVENTION

The placenta controls fetal development during pregnancy, being a semi-permeable barrier that controls the exchange of nutrients and wastes. See Hay, Harm. Res., 42 (4-5), 215-222 (1994); Jones et al., Placenta, 28 (8-9), 763-774 (2007); Guttmacher et al., Placenta, 35(5), 303-304 (2014); Cao et al., Neoreviews, 15(12), e537-e545 (December 2014); and Kaiser, Science, 344 (6188), 1073 (Jun. 6, 2014). Placental dysfunction is associated with increased perinatal and neonatal mortality and lifelong health complications in the mother and child. But the placenta remains one of the least understood organs in the human body. Guttmacher et al., Placenta, 35(5), 303-304 (2014), partly because a lack of human placenta-representative in vitro and in vivo models make it difficult to study this dynamic organ. Pasca & Penn, Neoreviews, 11(2), e64-e77 (February 2010).

According to the Center for Disease Control, fewer than 10% of pharmaceuticals have enough information on risks to a developing fetus. Meanwhile, nine out of ten women in the United States take at least one medication throughout pregnancy (Center for Disease Control). Many chronic conditions, such as epilepsy, high blood pressure, asthma, and depression, require medications that a woman cannot stop during her pregnancy. Conditions such as gestational diabetes and preeclampsia can arise during pregnancy requiring further medical intervention. Unfortunately, the techniques for assessing placental function are highly qualitative, such as histology and other descriptive methods. Pasca & Penn, Neoeviews, 11(2), e64-e77 (2010). The techniques have no capability for the rapid quantification of pharmaceutical interaction with the placenta, resulting in little quantified information on the environmental toxicant impact on placental structure and health.

Animal models cannot mimic the human placenta due to differences in the placental cell phenotype. Primary trophoblasts (which form the embryo-derived portion of the placenta) can be used, but these cells have a finite proliferative ability, limiting experiment time. Knöfler, Int. J. Dev. Biol., 54(2-3), 269-280 (2010). Choriocarcinoma cell lines provide information on hormonal changes during pregnancy, but there is significant variability in clone types. Orendi et al., Placenta, 32 Suppl, S49-54 (2011).

Lipid bilayers have been used to model biological interfaces. Lipid bilayers have been used to model the liver, red blood cells, myelin, mitochondria, endoplasmic reticula, and E. coli cell membranes. Alberts et al., The Lipid Bilayer, in Molecular Biology of the Cell, 4$^{th}$ edition (Garland Science, 2002); Berben et al., Eur. J. Pharm. Sci., 119, 219-233 (Jul. 1, 2018). Synthetic lipid membranes are used commercially to screen for intestinal drug absorption. Studies have compared these models to the CACO-2 cell line. Lipids function importantly in biological tissues and cells, having structural and barrier properties, energy storage, signaling, and protein aggregation. A lipid-based placental mimic could be a screening tool for molecular interactions in the placenta.

There is a need in the heterogeneous membrane art for human placenta-representative in vitro and in vivo models. Cell-free models of the placental bilayer do not currently exist. High-throughput molecular interaction screening models of the placenta do not now exist. A thorough comparison of lipids extracted from placental cell lines and tissues has not yet been reported. Thus, there is a need in the heterogeneous membrane art for lipid bilayer systems that can be used as tools to quantify placental interactions at the molecular scale.

SUMMARY OF THE INVENTION

The invention provides a lipid bilayer mimicking the lipid composition of the placenta. The lipid composition provides an in vitro placenta model using the lipid composition of the placental cell membrane. The invention provides lipid bilayer systems useful as tools to quantify pharmaceutical or environmental toxicant interactions with the placenta at the molecular scale, as shown in FIG. 13. By using this invention to improve understanding of the placenta, the medical field can minimize the risks to a developing fetus, better inform treatment plans, and screen new therapies. Ultimately, this placenta mimicking bilayer system is a useful tool for a rapid understanding of how medications may interact with the maternal-fetal interface, affecting prenatal, and future maternal health.

In the first embodiment, the invention provides in vitro cell-free placenta models that mimic the lipid composition of the placental cell membrane at different times during pregnancy. These in vitro cell-free placenta models provide for the rapid screening of molecular-scale interactions of molecule interactions with the maternal-fetal interface, as shown in FIG. 1. The in vitro cell-free placenta models enable rapid analysis of pharmaceuticals, environmental toxicants, and toxins for their potentially detrimental impact on the placenta, and thus, on prenatal and future maternal health.

In a second embodiment, the invention provides in vitro cell-free placenta models constructed from a reported composition. These in vitro cell-free placenta models comprise synthetic lipid vesicles, a synthetic lipid bilayer, or both synthetic lipid vesicles and synthetic lipid bilayer. These models contain the most abundant lipids in the placenta. The inventors developed a parallel artificial membrane permeability assay (PAMPA) with the placental compositions.

In a third embodiment, the invention provides in vitro cell-free placenta models constructed from trophoblast cell line-extracted lipids. These in vitro cell-free placenta models comprise lipid bilayers. This embodiment of in vitro cell-free placenta models is useful for comparing a synthetic lipid bilayer with a natural lipid bilayer. The inventors extracted and analyzed lipids from placental cell lines and cells. The inventors extracted the lipid composition from HTR-8 (which represents first-trimester trophoblast cells), TCL-1 (which represents third-trimester trophoblast cells), and primary trophoblast cells. Then, the inventors quantified the composition of the most abundant lipid classes, including phosphatidylcholine (PC), phosphoethanolamine (PE), phosphatidylinositol (PI), phosphatidylserine (PS), and sphingomyelin (SPH). The lipid composition of HTR-8 cells, TCL-1 cells, and primary trophoblasts exhibited statistically significant differences among the cells. See FIG. 1. Next, the inventors developed synthetic lipid vesicles with the same lipid composition as the HTR-8 and TCL-1 cells. The inventors confirmed the hydrodynamic diameter of the trophoblast lipid vesicles. See, FIG. 2. Thus, the inventors have successfully fabricated lipid bilayers mimicking the lipid composition of placental cells.

In a fourth embodiment, the invention provides methods of testing compounds for interactions with the placenta at the molecular scale. The invention provides methods of testing pharmaceuticals or environmental toxicants for interactions with the placenta. The steps of the methods are provided in this specification or by adapting steps from methods using non-placental in vitro models.

BRIEF DESCRIPTION OF THE DRAWINGS

FIG. 1 shows the composition of the major lipid classes relative to each other. The lipid composition of HTR-8 cells, TCL-1 cells, and primary trophoblast cells exhibited statistically significant differences among the cells. The inventors measured significant differences in phosphatidylcholine (PC), phosphatidylethanolamine (PE), phosphatidylinositol (PI), and phosphatidylserine (PS) compositions among the bilayers from the several cell types. The statistical analyses were performed using two-way ANOVA with Tukey posthoc analysis; $a=0.05$; $p<0.01$; $*p<0.001$; $****p<0.0001$.

DETAILED DESCRIPTION OF THE INVENTION

Industrial Applicability

Figure 1:
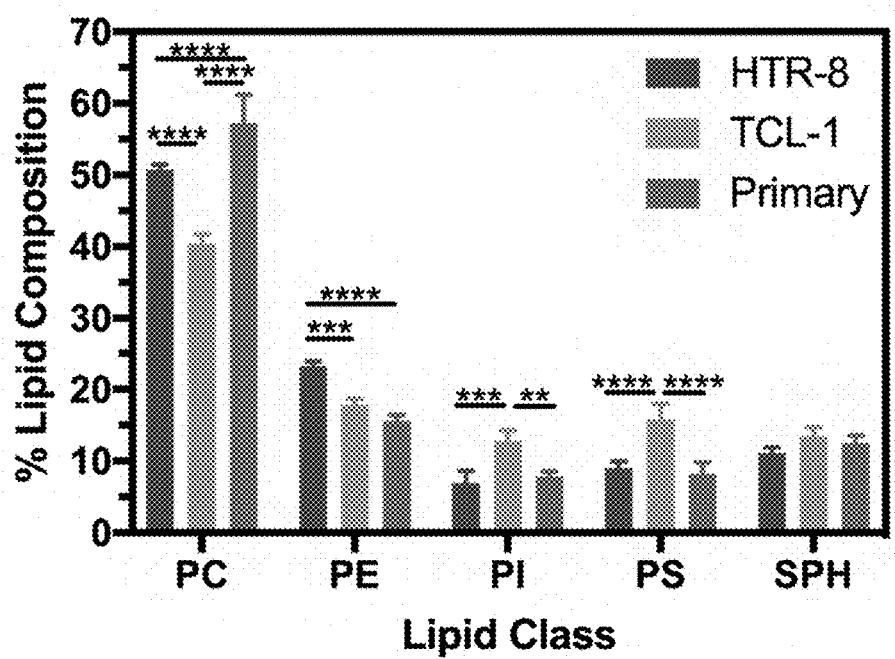
FIG. 1 is a set of bar graphs showing the results from a characterization of and quantization of major lipid classes of placental lipids from HTR-8 cells, TCL-1 cells, and primary placental cells.

During a woman's pregnancy, many molecules come in contact with her placenta, e.g., pharmaceuticals and environmental toxins (such as phthalates). Women exposed to high concentrations of di-(2-ethylhexyl) phthalate (DEHP) are 60% more likely to lose a pregnancy compared to women with lower levels of DEHP. Messerlian et al., Epidemiology (Cambridge, Mass.), 27(6), 879 (2016). Although 90% of women take at least one medication throughout their pregnancies, fewer than 10% of FDA-approved medications have sufficient data on their risks when used during pregnancy. Center for Disease Control, Treating for Two Program.

No rapid quantification methods exist to measure how pharmaceuticals interact with the placenta. There is little quantified information on how environmental toxins may affect the placental structure and health.

The inventors developed lipid vesicles and bilayers mimetic of the placental trophoblast composition. They quantified the lipid composition of HTR-8, TCL-1, and primary trophoblast cells, which are representative for first, third, and term placenta, respectively. Using this composition, the inventors develop synthetic vesicles, supported bilayers, and suspended bilayers. Vesicles were prepared using the dry lipid film and extrusion technique and were quantified to have a hydrodynamic diameter of 100 nm with low polydispersity and varying degrees of negative charge. The inventors then used quartz crystal microbalance with dissipation monitoring (QCM-D) to rupture the vesicles on a silica substrate using an α-helical (AH) peptide to induce vesicle rupture. Next, the inventors developed suspended trophoblast bilayers to perform transport studies and compare these results with transport across trophoblast cells. The goal was to characterize and develop these structures, then test the application of them. Test molecules including di(2-ethylhexyl) phthalate (DEHP), a common plasticizer and potential environmental toxicant, amphotericin B, a commonly used antifungal, and amBisome®, the liposomal formulation of amphotericin B, were investigating for how they interact with the trophoblast bilayers. The inventors observed that amphotericin B interacts less with both the supported and suspended trophoblast bilayers compared to amBisome®. Ultimately, these lipid bilayers can serve as a platform for quicker initial screenings of how molecules may interact with the maternal-fetal interface to better determine the next steps for testing.

This invention provides lipid bilayer systems to use as a tool to quantify these interactions at the molecular scale. This tool can be used for adsorption and permeation studies of small molecules with the placenta lipid bilayer.

Some companies sell parallel artificial membrane permeability assays (PAMPA) where a lipid bilayer is coated on a porous insert. These non-specific lipid bilayers are nevertheless used for high-throughput testing of how compounds behave with cell membranes. By improving understanding of the placenta through this invention, the lessons learned from non-placental membranes can transfer to the study of the human placenta.

These results quantified the lipid composition of trophoblast cells at various time points during pregnancy. The inventors observed significant differences in compositions comparing first, third, and term trophoblasts. Using these compositions, the inventors next developed the first synthetic lipid vesicles and bilayers with representative trophoblast lipid distributions. After the characterization of developing these structures, the inventors then used these structures to investigate interactions of DEHP, amphotericin B, and amBisome®. DEHP adsorbed to all three of the bilayers, which can have the potential to influence transport properties across the interface. Amphotericin B interacted more with both supported and suspended bilayers compared to amBisome®. This result suggests that the delivery vehicle of a pharmaceutical should be considered for treatment needs during pregnancy. The inventors observed similar interaction trends between the bilayers and trophoblast monolayers, indicating the correlation of the model. Ultimately, these results provide a platform that can now test a variety of environmental toxicants and pharmaceuticals. This system can be useful for quantifying many other small molecules in a high-throughput manner. This system allows for a first screening tool to provide information on what the next tests should be performed to understand risks during pregnancy fully.

Definitions

For convenience, the meaning of some terms and phrases used in the specification, examples, and appended claims, are below. Unless stated otherwise or implicit from context, these terms and phrases have the meanings below. These definitions are provided to aid in describing particular embodiments and are not intended to limit the claimed invention. Unless otherwise defined, all technical and scientific terms have the same meaning as commonly understood by people having ordinary skill in the heterogeneous membrane art. If there is an apparent discrepancy between the usage of a term in the art and its definition provided in this specification, the meaning provided in this specification shall prevail.

"Amphotericin B" antifungal medication is used for severe fungal infections and leishmaniasis. World Health Organization, "Control of the leishmaniasis: report of a meeting of the WHO Expert Committee on the Control of Leishmaniases." (March 2010). Amphotericin B is in the polyene class of medications and works in part by interfering with the cell membrane of the fungus. Amphotericin B is on the World Health Organization's List of Essential Medicines, the most effective and safe medicines needed in a health system. World Health Organization, "WHO Model List of Essential Medicines (19th List)" (April 2015).

"BeWo" human cell line is the first human, trophoblastic endocrine cell type to be maintained in continuous culture. This cell line was initiated from malignant gestational choriocarcinoma of the fetal placenta. BeWo cells secrete placental hormones, including chorionic gonadotrophin (hCG), polypeptide hormones, lactogen, estrogenic and progestational steroids, estrone, estradiol, estriol, and progesterone. Cellular differentiation of this stem cell type occurs when hormonal precursors are added to the medium. Due to the high glycolytic activity, the cells must be sub-cultured or supplied with fresh media every 24-48 hours to prevent glucose exhaustion. BeWo cells are commercially available from Millipore-Sigma (Burlington, MA, USA), Product No. 86082803.

"CACO-2" cell line is a continuous line of different human epithelial colorectal adenocarcinoma cells, developed by the Sloan-Kettering Institute for Cancer Research. Although derived from a colon carcinoma, when cultured under specific conditions, CACO-2 cells become differentiated and polarized. Their phenotype, morphologically and functionally, resembles the enterocytes lining the small intestine. CACO-2 cells are commercially available.

"di(2-ethylhexyl) phthalate" (DEHP) is an organic compound with the formula $C_6H_4(CO_2C_8H_{17})_2$. DEHP is a phthalate, being the diester of phthalic acid and the branched-chain 2-ethylhexanol. DEHP is a commonly used plasticizer in many household products. DEHP can easily leach from plastics leading to it becoming an environmental toxicant. Recent studies have shown that acquiring higher concentrations of phthalates, such as DEHP, increases the risk for miscarriage.

"Differential ion mobility system suitability." Ion-mobility spectrometry (IMS) is an analytical technique used to separate and identify ionized molecules in the gas phase based on their mobility in a carrier buffer gas. The method also has many laboratory analytical applications, including the analysis of both small and large biomolecules.

"HTR-8" is a first-trimester human trophoblast cell line established by immortalizing a physiologic extravillous trophoblast cell by transfection with a plasmid containing the simian virus 40 large T antigen (SV40). See Graham et al., Exp. Cell Res., 206(2), 204-11. (June 1993). These cells grow as a thin layer of ectoderm. HTR8/SVneo cells are commercially available from the American Type Culture Collection (Manassas, VA, USA) as ATCC® CRL 3271™.

"Liquid chromatography-mas spectroscopy" (LC-MS). In high-pressure liquid chromatography (HPLC), a liquid sample is injected into a stream of solvents. Together, the sample and solvents are forced, at high pressure, through an analytical column. Depending on the column and solvents, some chemicals exit the column at different times. At the end of the column are an ultraviolet (UV) light source and a photodetector. When an appropriate wavelength is selected, the analyte can be detected by a change in absorbance as it exits the column. The absorbance is plotted over time. See, Karger, "HPLC: Early and recent perspectives," J. Chem. Ed., 74(1), 45 (1997). People having ordinary skill in the chemical laboratory art can supplement HPLC methods with other analytical techniques such as mass spectrometry. Zeng & Kassel, "Developments of a fully automated parallel HPLC/mass spectrometry system for the analytical characterization and preparative purification of combinatorial libraries," Analytical Chemistry, 70(20), 4380-4388 (1998); Shockcor et al., "Combined HPLC, NMR spectroscopy, and ion-trap mass spectrometry with application to the detection and characterization of xenobiotic and endogenous metabolites in human urine," Analytical Chemistry, 68(24), 4431-4435 (1996). Mass spectrometry (MS) is an analytical technique that ionizes chemical species and sorts the ions based on their mass-to-charge ratio. A mass spectrum measures the masses within a sample. Mass spectrometry is useful for broad and high-throughput metabolic screening. Zampieri et al., Current Opinion in Chem. Bio. 36, 15-23 (2017). Advances in statistical tools and databases support mass spectrometry. Brown et al., Analyst, 134(7), 1322-32 (2009); Wishart et al., Nucleic Acids Res. 4(46), 608{617 (2018). Sub-zeptomole mass spectrometry and nanomolar concentration detection have been available for nearly two decades. Belov et al., Anal. Chem. 72(10), 2271-2279 (2000); Tang et al., J. Bact. 189, 940-949 (2007). In this specification, LC-MS experiments used Thermo Surveyor MS pump and Thermo Micro AS sampler, and Waters Sunfire C18, 5-mm, 2.1×50 mm HPLC column. Mobile phases were prepared as: (A) 60:40 (v/v) acetonitrile:water with ten mM ammonium formate, (B) 90:10 (v/v) isopropanol:acetonitrile with ten mM ammonium formate. The gradient started at 35% B and increased to 95% B in sixty minutes. The HPLC system was coupled to Thermo LZ+XQ linear ion trap mass spectrometer, equipped with an electrospray ionization source. The HPLC effluent was detected in negative ionization mode, with consecutive full scan MS and tandem MS/MS experiments. The identification of the individual phospholipid molecular species was based on their m/z values and analysis of the production spectra produced from collision-induced dissociation (CID) fragmentation. After the major lipid species, m/z values were identified, the inventors obtained extracted ion chromatograms (EIC's). They integrated the area under the curve (AUC) to determine the abundance of the lipid ion. Results of semi-quantitation of phospholipids used full scan LC-MS are expressed as relative abundance in percentage (mean±SD). In this specification, the Lipidomix® kit, purchased from Avanti Polar Lipids (Alabaster, AL, USA), was being used to determine the composition of the total major lipid classes within the samples. The Differential Ion Mobility System Suitability Lipidomix® system provides premixed synthetic lipid standards combined with a natural lipid extract to provide a system suitability standard that allows you to confirm visualization and separation of each lipid class.

"Parallel artificial membrane permeability assay" (PAMPA) is a method that determines the permeability of substances from a donor compartment, through a lipid-infused artificial membrane into an acceptor compartment. A multi-well microtiter plate is used for the donor, and a membrane/acceptor compartment is placed on top. The whole assembly is referred to in the heterogeneous membrane art as a "sandwich." Initially, the drug is added to the donor compartment, and the acceptor compartment is drug-free. After an incubation period, which may include stirring, the sandwich is separated, and the drug is measured in each compartment. Techniques including but not limited to absorbance measurements allow calculation of the drug that remains in the membrane.

"Quartz crystal microbalance with dissipation" (QCM-D) monitors frequency changes ($\Delta F$) and dissipation changes ($\Delta D$) on quartz QCM-D substrates over time and in real-time. Changes in frequency correspond to the oscillation of the piezoelectric quartz crystal (with a fundamental frequency of five MHz) sandwiched between gold electrodes, over which an alternating voltage is applied. Changes in frequency are inversely related to mass changes on the surface. Dissipation changes are measured when the applied voltage is turned off, and the dampening of the acoustic waves is monitored. These energy dissipations changes monitor the viscoelasticity of the sensor-adsorbed material.

"TCL-1" cell line (Trophoblast Cell Line-1) is a tool to study trophoblast biology The cell line was established by retroviral expression of simian virus 40 large T antigen, by Lewis et al., Placenta 17, 137-146 (1996). The TCL-1 cell line is more resilient than the cultures of primary trophoblast cells, including extended lifespans in culture. It is thus advantageous for studies encompassing more detailed investigations of trophoblast function and molecular biology.

"Trophoblast" is a cell from the layer of tissue on the outside of a mammalian blastula, supplying the embryo with nourishment and later forming the major part of the placenta. See, New Oxford American Dictionary.

Enabling References

People having ordinary skill in the heterogeneous membrane art can use one or more of these patents and publications as guidance to predictable results when making and using the invention.

U.S. Pat. No. 8,986,781 (Chen et al.) "Immobilized multilayer artificial membrane for permeability measurements (PAMPA)." This patent provides an example of artificial membranes, but the exemplary composition is not placental-specific. The patent shows one method of using the composition as a permeability tool for drug permeability screening. The disclosure allows for filter membranes to mimic the structure of a biological membrane, though not the placenta. The filter membrane of the disclosure can have a hydrophobic interior and hydrophilic surfaces. The patent disclosed a film of "sticky" compounds to reduce retention, thus improving the measurement of "sticky" compounds. The compounds were added to several organic solvents used in a buffer, thus increasing the solubility of certain compounds. The film retains its integrity and thus to improve the ability to measure the permeability of low solubility compounds.

This patent does not mention preparing membranes that could mimic a placental membrane.

U.S. Pat. No. 9,956,252 (Tseng et al.), "Purified Amniotic Membrane Compositions and Methods of Use": This patent relates to compositions and methods for modulating cellular physiology and pathological processing using a combination of compounds that can be found in amniotic membrane preparations. The purified compositions comprise at least four components: Cross-linked high molecular weight hyaluronan (HA); Tumor necrosis factor-stimulated gene 6 (TSG-6); Pentraxin (PTX-3); and Thrombospondin (TSP-1). While this disclosure relates to mammalian tissues, including the placenta, it does not deal with studying the effect and permeation of pharmaceutical drugs and other chemicals on the placenta.

Alberts et al., "The Lipid Bilayer." in Molecular Biology of the Cell, 4th ed. (New York: Garland Science, 2002. Molecular Biology of the Cell is the classic in-depth text reference in cell biology. By extracting fundamental concepts and meaning from this enormous and ever-growing field, the authors tell the story of cell biology and create a coherent framework through which non-expert readers may approach the subject.

Aengenheister et al., "An Advanced Human in Vitro Co-Culture Model for Translocation Studies across the Placental Barrier." Sci. Rep., 8(1), 1-12 (2018).

Baig et al., "Lipidomic Analysis of Human Placental Syncytiotrophoblast Microvesicles in Adverse Pregnancy Outcomes." Placenta, 34 (5), 436-442 (2013).

Bailey et al., "Effects of Flow and Bulk Vesicle Concentration on Supported Lipid Bilayer Formation. Langmuir 2017, 33 (43), 11986-11997.

Berben et al., "Drug Permeability Profiling Using Cell-Free Permeation Tools: Overview and Applications. Eur. J. Pharm. Sci., 119, 219-233 (2018).

Bermejo et al., "PAMPA—a Drug Absorption in Vitro Model: 7. Comparing Rat in Situ, Caco-2, and PAMPA Permeability of Fluoroquinolones." Eur. J. Pharm. Sci., 21 (4), 429-441 (2004).

Bligh & Dyer, "A Rapid Method of Total Lipid Extraction and Purification. Can. J. Biochem. Physiol. 1959, 37 (8), 911-917.

Blundell et al., "Placental Drug Transport-on-a-Chip: A Microengineered In Vitro Model of Transporter-Mediated Drug Efflux in the Human Placental Barrier." Adv. Healthc. Mater., 7 (2), 1-9 (2018).

Bode et al., "In Vitro Models for Studying Trophoblast Transcellular Transport." Methods Mol. Med., 122, 225-239 (2006).

Brown et al., "A Lipidomic Analysis of Placenta in Preeclampsia: Evidence for Lipid Storage," PLoS One, 11(9): e0163972 (Sep. 29, 2016). This scientific publication shows the extraction of lipids from the term placenta. The publication does not disclose the use of the extracted lipids to develop an artificial placenta lipid bilayer.

Cao et al., "Placental Microbiome and Its Role in Preterm Birth." Neoreviews, 15(12) (2014). The placenta controls fetal development during pregnancy, being a semi-permeable barrier that controls the exchange of nutrients and wastes.

Cho et al., "Alpha-Helical Peptide-Induced Vesicle Rupture Revealing New Insight into the Vesicle Fusion Process As Monitored in Situ by Quartz Crystal Microbalance-Dissipation and Reflectometry." Anal. Chem., 81 (12), 4752-4761 (2009).

Cho et al., "Employing an Amphipathic Viral Peptide to Create a Lipid Bilayer on Au and TiO2." J. Am. Chem. Soc., 129(33), 10050-10051 (2007).

Guttmacher et al., "The Human Placenta Project: Placental Structure, Development, and Function in Real Time." Placenta 2014, 35 (5), 303-304 (2014). The placenta controls fetal development during pregnancy, being a semi-permeable barrier that controls the exchange of nutrients and wastes.

Hardy et al., "Biomimetic Supported Lipid Bilayers with High Cholesterol Content Formed by α-Helical Peptide-Induced Vesicle Fusion." J. Mater. Chem., 22 (37), 19506-19513 (2012).

Hardy et al., "Model Cell Membranes: Techniques to Form Complex Biomimetic Supported Lipid Bilayers via Vesicle Fusion." Curr. Opin. Colloid Interface Sci., 18(5), 448-458 (2013).

Haw Zan et al., Peptide-Mediated Formation of Charged Planar Lipid Bilayers." J. Phys. Chem. B, 118, 41 (2014).

Huang et al., "Increased Placental Phospholipid Levels in Pre-Eclamptic Pregnancies." Int. J. Mol. Sci., 14 (2), 3487-3499 (2013). This scientific publication shows the extraction of lipids from the term placenta. This scientific publication does not disclose the use of the extracted lipids to develop an artificial placenta lipid bilayer.

Hubatsch et al., "Determination of Drug Permeability and Prediction of Drug Absorption in Caco-2 Monolayers." Nat. Protoc., 2 (9), 2111-2119 (2007).

Kaiser, "Gearing up for a Closer Look at the Human Placenta." Science, 344 (6188), 1073 (Jun. 6, 2014). The placenta controls fetal development during pregnancy, being a semi-permeable barrier that controls the exchange of nutrients and wastes.

Kalkunte et al., "In Vitro and In Vivo Evidence for Lack of Endovascular Remodeling by Third Trimester Trophoblasts." Placenta, 29, 871-878 (October 2008).

Kamiński, "Recent Progress in the Study of the Interactions of Amphotericin B with Cholesterol and Ergosterol in Lipid Environments." Eur. Biophys. J. 43 (10-11), 453-467 (2014).

Keller & Kasemo, "Surface Specific Kinetics of Lipid Vesicle Adsorption Measured with a Quartz Crystal Microbalance." Biophys. J., 75 (3), 1397-1402 (1998).

Korkes et al., Lipidomic Assessment of Plasma and Placenta of Women with Early-Onset Preeclampsia." PLoS One, 9 (10), e110747 (2014).

Lee et al., "Placenta-on-a-Chip: A Novel Platform to Study the Biology of the Human Placenta." J. Matern. Fetal. Neonatal Med., 29 (7), 1046-1054 (2016).

Masungi et al., "Parallel Artificial Membrane Permeability Assay (PAMPA) Combined with a 10-Day Multiscreen Caco-2 Cell Culture as a Tool for Assessing New Drug Candidates." Pharmazie, 63(3), 194-199 (2008).

Messerlian et al., "Urinary Concentrations of Phthalate Metabolites and Pregnancy Loss among Women Conceiving with Medically Assisted Reproduction." Epidemiology, 27 (6), 879-888 (2016).

Muoth et al., "A 3D Co-Culture Microtissue Model of the Human Placenta for Nanotoxicity Assessment." Nanoscale, 8 (39), 17322-17332 (2016).

Paglia & Coustan, "The Use of Oral Antidiabetic Medications in Gestational Diabetes Mellitus." Curr. Diab. Rep., 9(4), 287-290 (2009).

Pasca & Penn, "The Placenta: The Lost Neuroendocrine Organ." Neoreviews, 11(2) (2012). The techniques for assessing placental function include histology and other descriptive methods.

Piazza & Urbanetz, "Environmental Toxins and the Impact of Other Endocrine Disrupting Chemicals in Women's Reproductive Health." JBRA Assist. Reprod., 23 (2), 154-164 (2019).

Pichler & Emmerstorfer-Augustin, "Modification of Membrane Lipid Compositions in Single-Celled Organisms—From Basics to Applications." Methods, 147, 50-65 (September 2018).

Pilmis et al., "Antifungal Drugs during Pregnancy: An Updated Review. J. Antimicrob. Chemother. 2015, 70 (1), 14-22.

Richter & Brisson, "Following the Formation of Supported Lipid Bilayers on Mica: A Study Combining AFM, QCM-D, and Ellipsometry." Biophys. J., 88 (5), 3422-3433 (2005).

Schettler, "Human Exposure to Phthalates via Consumer Products." Int. J. Androl. 2006, 29, 134-139.

Schmidt et al., "Only Humans Have Human Placentas: Molecular Differences between Mice and Humans." J. Reprod. Immunol., 108 (2015), 65-71 (2015).

Shy & Wkh, "Cell Types of Placenta." Vasc. Biol. Placenta, 1-9 (2016).

Sibley et al., "Knowledge Needed about the Exchange Physiology of the Placenta." Placenta, 64, S9-S15 (2018).

Takao et al., "Isolation and Characterization of Human Trophoblast Side-Population (SP) Cells in Primary Villous Cytotrophoblasts and HTR-8/SVneo Cell Line." PLoS One, 6 (7), e21990 (2011).

Van Meer et al., "Membrane Lipids: Where They Are and How They Behave." Nature Reviews Molecular Cell Biology, 9, pages 112-124 (February 2008). Throughout the biological world, a 30 Å hydrophobic film typically delimits the environments that serve as the margin between life and death for individual cells. Biochemical and biophysical findings provided a detailed model of the composition and structure of membranes, which includes levels of the dynamic organization both across the lipid bilayer (lipid asymmetry) and in the lateral dimension (lipid domains) of membranes. This review assesses how cells apply anabolic and catabolic enzymes, translocases, and transporters, plus the intrinsic physical phase behavior of lipids and their interactions with membrane proteins, to create the unique compositions and multiple functionalities of their membranes.

Von Dadelszen & Magee, "Antihypertensive Medications in Management of Gestational Hypertension-Preeclampsia." Clin. Obstet. Gynecol., 48 (2), 441-459 (2005).

Zan et al., "Peptide-Mediated Formation of Charged Planar Lipid Bilayers." J. Phys. Chem. B, 118(13), 3616-3621 (2014).

Zan et al., "Rupture of Zwitterionic Lipid Vesicles by an Amphipathic, α-Helical Peptide: Indirect Effects of Sensor Surface and Implications for Experimental Analysis." Colloids Surfaces B Biointerfaces, 121, 340-346 (2014).

Center for Disease Control, Treating for Two: Medicine and Pregnancy. https://www.cdc.gov/pregnancy/meds/treatingfortwo/index.html.

The following EXAMPLES are provided to illustrate the invention and should not be considered to limit its scope.

Example 1

Synthetic Placenta Lipid Membranes for Nanomaterial Interaction Studies

Rationale. The goal of this EXAMPLE 1 is to provide an in vitro system to monitor molecular interactions with a synthetic placental bilayer. A supported lipid bilayer (SLB) was developed from synthetic lipids mimicking the placenta cell membrane for adsorption and mass loss studies. Supported lipid bilayers are a useful tool to investigate adsorption or mass removal interactions occurring. To gain more information, the inventors developed suspended lipid bilayers across PVDF porous inserts. This development produced a parallel artificial membrane permeability assay (PAMPA) to investigate further DEHP, amphotericin B, and amBisome® interactions with HTR-8, TCL-1, and primary lipid models. The PAMPA studies can be used for permeation.

Analytical approach. First, the inventors used a reported composition to develop placental lipid bilayers. Previous studies have extracted lipids from placental tissue and analyzed the abundance of each lipid. Huang et al., Int. J. Mol. Sci., 14 (2), 3487-3499 (2013); Baig et al., Placenta, 34 (5), 436-442 (2013). The inventors developed uni-lipid supported lipid bilayers. See, Bailey et al., Langmuir, 33 (43), 11986-11997 (2017). The inventors are also producing a more sophisticated system containing multiple lipids and cell membrane components.

Second, the inventors used cholesterol (CH), phosphatidylcholine (PC), phosphatidylethanolamine (PE), and sphingomyelin (SPH) with a composition of 36%, 32%, 21%, and 11% v/v, respectively, to develop a placental lipid bilayer model.

Complete PAMPA development. The inventors are also forming lipid bilayers for parallel artificial membrane permeability assays (PAMPA), where a solution of the lipids is applied to a permeable membrane insert, such as a Transwell insert. The lipids undergo self-assembly across the insert pores. The inventors are characterizing the bilayer using Raman spectroscopy, which provides a structural fingerprint by the inelastic scattering of light from a laser source. See, Czamara et al., J. Raman Spectrosc., 46(1), 4-20 (2015).

With these two synthetic placenta lipid membrane models, people having ordinary skill in the heterogeneous membrane art can study molecular adsorption on QCM-D supported lipid bilayer (SLB). People having ordinary skill in the heterogeneous membrane art can study permeation through the bilayer (PAMPA).

Folic acid and carbofuran interactions. The inventors are testing the adsorption and permeation of the prenatal supplement folic acid and the common pesticide carbofuran. Folic acid should permeate the bilayer but not cause destabilization. Carbofuran is toxic against keratinocytes. Abhishek et al., Bioinformation, 10(12), 716-720 (Dec. 31, 2014). So, carbofuran may cause bilayer disruption.

The inventors are testing the adsorption and permeation of other small molecules, including DEHP, amphotericin B, amBisome®, caffeine, carbamazepine, warfarin, furosemide, folic acid, and methotrexate.

Third, the inventors also used chicken egg-derived PC for preliminary bilayer formation on Transwell for PAMPA. Raman spectroscopy confirmed formation showing several lipid specific peaks and homogeneity of the bilayer throughout the insert.

The inventors also investigated that the synthetic lipid vesicles have the expected compositions. Since these are complex vesicles with multiple lipids that can potentially form lipid rafts, the inventors wanted to ensure that some lipids were not remaining within the extruder and giving different compositions. A comparison between the lipid composition of the inventors' vesicles and the cell extracts demonstrated that the vesicles contain within 3% of the composition for all lipids and vesicle types.

Example 2

Trophoblast Cell Line-Derived Placental Lipid Vesicles and Lipid Bilayer

Rationale. The goal of this EXAMPLE 2 developed a lipid bilayer from trophoblast cell-extracted lipids. Trophoblast cells, specifically the BeWo villous trophoblast cell line, have been used to study maternal-fetal transport. Ali et al., Int. J. Pharm., 454(1), 149-157 (2013). The inventors are developing bilayers from the lipids extracted from the established BeWo villous trophoblast cell line. The inventors are comparing the bilayers with the synthetic composition from EXAMPLE 1.

Analytical approach. Lipid extraction from trophoblast cells. Quantification of lipids in BeWo trophoblast cells. The inventors first collected BeWo trophoblast cells, then solubilized and agitated the BeWo cell pellet. They next analyzed the lipid composition by gas chromatography. The lipid extracts are processed through the dry lipid film method and extrusion, as performed in EXAMPLE 1.

Cell-derived lipid vesicle and bilayer development. Lipid vesicles can be characterized using cryo-transmission electron microscopy (TEM) and DLS. QCM-D can monitor bilayer formation with these natural lipid vesicles.

Complete PAMPA development. PAMPA is also being developed using the solubilized BeWo trophoblast cell lipid extract. The extracted lipids are coated onto Transwell inserts. Raman spectroscopy can identify the lipid fingerprint of the insert. See, Czamara et al., J. Raman Spectrosc., 46 (1), 4-20 (2015). Previous studies have shown that BeWo cell extracts can form a monolayer on an insert. Orendi et al., Reproduction, 140(5), 759-766 (2010). Before cell seeding, placental collagen is used to coat the surface of the Transwell insert. BeWo trophoblast cells have been cultured and seeded onto Transwell porous membranes, where the inventors demonstrated uniform cell growth on the Transwell insert.

The cell-derived lipid vesicle size is similar to the synthetic vesicles. Placental vesicles showed an average size of 149±1.5 nm and a polydispersity index of 0.078±0.015 (n=3), as characterized via dynamic light scattering (DLS). Because the synthetic vesicles contain only the most abundant lipids, some slight size difference is observed. The most abundant lipids should control adsorption and permeation, so the models developed in this EXAMPLE have similar results to the synthetic bilayer from EXAMPLE 1.

Molecular interactions with common small molecules. The inventors are studying how folic acid and carbofuran adsorb and permeate the cell-derived placental lipid bilayer. This adsorption and permeation are being compared to trophoblast cells grown on Transwell inserts and also the synthetic placental lipid bilayer. Comparing the lipid bilayer model to the BeWo cells cultured on the Transwell is important for informing the use of these model bilayers in place of cell-containing models for placenta-drug interaction studies.

The inventors are studying how other small molecules adsorb and permeate the cell-derived placental lipid bilayer. Examples of other small molecules include DEHP, amphotericin B, amBisome®, caffeine, carbamazepine, warfarin, furosemide, and methotrexate.

Example 3

Tissue-Derived Placental Lipid Vesicles and Lipid Bilayer

Rationale. The goal of this EXAMPLE 3 is to extract the lipid composition from placental tissue, quantify this extract, and use it to develop placental lipid bilayers. This aim is also to allow comparison of the lipid composition with the placental cell lines, which has not previously been investigated.

Analytical approach. Lipid extraction from placenta tissue. Quantification of lipids in placenta tissue. The Women & Infants Hospital of Rhode Island kindly provided human placenta tissue samples to the inventors obtain for them to homogenize. The homogenized tissue is processed similarly to the processing of the BeWo cells, to extract the lipids using liquid-liquid extraction. The extracted lipids then went through the dry thin-film method and extrusion described in EXAMPLE 1 to obtain placental tissue-derived lipid vesicles. Both supported lipid bilayers and PAMPA are formed and characterized by the methods described in EXAMPLE 1 and EXAMPLE 2.

Molecular interactions with common small molecules. The adsorption and permeation of folic acid and carbofuran are being studied and compared to the bilayers formed in EXAMPLE 1 and EXAMPLE 2.

This placental tissue-derived lipid bilayer is the most representative of the placenta lipid bilayer structure. The inventors are comparing the similarities and differences of the placental tissue-derived lipid bilayer with the synthetic bilayer. The inventors can also model different disease states of the placenta by quantifying the lipids in the placenta complicated with conditions like preeclampsia and producing lipid bilayers from lipids extracted from such placenta.

Example 4

Development and Application of a Placental Lipid Bilayer for Cell-Free Molecular Interaction Studies; Characterization of Three Cell Lines That Represent Different Time Point During Pregnancy; Materials and Methods HTR-8 cells, TCL-1 cells, and primary trophoblast cell lines represent different time points during pregnancy. Their protein expression characterizes these three cell types. Takao et al., PLoS One, 6(7), e21990 (2011). They were not previously characterized for their lipid profile. By characterizing the lipid profile of these three placenta-representative cell lines, the inventors here establish differences in the lipid composition of the three cell types, which indicate differences in lipid composition at the various stages of pregnancy.

The inventors observed differences in the fatty acid distributions within each lipid class. See, FIG. 11). FIG. 1 shows the composition of the major lipid classes relative to one another. The inventors observed significant differences in phosphatidylcholine (PC), phosphatidylethanolamine (PE), phosphatidylinositol (PI), and phosphatidylserine (PS) composition between HTR-8, TCL-1, and primary bilayers. Interestingly, the TCL-1 composition has an increased amount of negatively charged lipids PI and PS, with a decreased amount of zwitterionic PC compared to the HTR-8 and primary compositions.

Here the inventors indicate the lipid composition of specifically trophoblast cells. Trophoblast cells, particularly villous trophoblast cells, are responsible for the nutrient and waste transport across the placenta. By mimicking this composition, the inventors focus on the lipids responsible for transportation, which is a goal of this invention. Trophoblast cells are dynamic and change the course of pregnancy.

HTR-8 cells represent first-trimester trophoblasts. TCL-1 cells represent third-trimester trophoblasts. The Women & Infants Hospital Kilguss Research Institute kindly donated cells from the HTR-8 cell line and the TCL-1 cell line to the inventors. The inventors cultured the TCL-1 cells and the HTR-8 cells in Rosewell Park Memorial Institute (RPMI) medium 1640 (Gibco, Waltham, MA, USA) supplemented with 10% (v/v) Fetal Bovine Serum (FBS) (Corning Incorporated, Corning, NY, USA) and 1% (v/v) penicillin-streptomycin) at 37° C. under 5% $CO_2$.

Primary trophoblast cells represent the term placenta. The inventors purchased human primary trophoblasts from ScienCell Research Laboratories (Carlsbad, CA, USA). The inventors cultured the human primary trophoblasts in RPMI 1640 medium (GIBCO, 11875, MA, USA) supplemented with 10% FBS, 100 U/ml penicillin, and 100 µg/ml streptomycin (GIBCO, 15140) at 37° C. in a 5% $CO_2$ atmosphere.

Unless otherwise stated, the inventors purchased all chemicals used in these EXAMPLES from Sigma-Aldrich (St. Louis, MO, USA). For all syntheses and assays, the inventors used milli-Q water (18.2 MΩ) from EMD Millipore (Taunton, MA, USA).

Lipid extraction and characterization of lipids from three cell types. The inventors extracted lipids from TCL-1 cells, HTR-8 cells, and primary trophoblast cells using the Bligh-Dyer procedure. Bligh et al., J. Biochem. Physiol., 37(8), 911-917 (1959). After cell passage, the inventors resuspended the cell pellets in one mL of MilliQ water. The inventors added 3.75 mL of a 1:2 v/v mixture of chloroform:methanol to the suspended cell pellet. The solution was vortexed for fifteen minutes. The inventors then added 1.25 mL of chloroform to the solution and mixed the liquids. The inventors added 1.25 mL of water and mixed the liquids for one minute, followed by centrifugation at 1,000 g for ten minutes. The bottom organic phase layer of the centrifuged liquid, where the lipids were, was removed to another container. Drying under a nitrogen gas stream removed the organic liquid. The inventors then quantified the remaining lipids. Three separate cell cultures were performed for each cell line. Three primary samples were used.

HTR-8 cell culture and TCL-1 cell culture on Transwell plates for comparison interaction studies. Transwell inserts (24-well plate, Corning 3470, Corning Incorporated, Corning, NY, USA) were prepared for trophoblast culture as described. Briefly, human placental collagen coating material was made by dissolving the collagen in 0.1% acetic acid, which was stored at 4° C. Before using, the stock of placental collagen was diluted 1:3 in 70% ethanol. In a 24-well plate insert, twenty-one µL was added to each well and dried for two hours. The plates were sterilized for 20 minutes under UV light before use. The wells were then hydrated in 1× phosphate-buffered saline (PBS) for thirty minutes. HTR-8 cells and TCL-1 cells were cultured, as described above. After passaging, 30,000 cells/mL were plated on the Transwell inserts.

Alexa Fluor 594 phalloidin (Life Technologies, Carlsbad, CA, USA) for actin cytoskeleton and 4',6-diamidino-2-phenylindole (DAPI) for nuclei immunocytochemistry was performed to observe the confluence of the TCL-1 and HTR-8 cell layers. Once confluent, transport studies with DEHP, amphotericin B, and amBisome® were performed similarly to 2.5 Suspended lipid bilayer interactions using parallel artificial membrane permeability assay (PAMPA). For these Transwell plates, the donor compartment was filled with 200 µL containing the small molecule of interest, and the acceptor compartment was filled with 500 µL containing 1% DMSO for DEHP and amphotericin B transport studies. The plates were incubated for two hours at 37° C. before absorbance measurements for DEHP, amphotericin B, and amBisome® at 280 nm, 340 nm, and 320 nm, respectively, using a plate reader (Cytation 3, BioTek, Winooski, VT, USA).

Assays were conducted in triplicate at a minimum. Representative results for the third overtone are shown in figures for all QCM-D $\Delta F$ and $\Delta D$ measurements unless otherwise specified. Results are given as mean±standard deviation. Statistical significance was calculated using Prism 7 (GraphPad) with one-way analysis of variance (ANOVA) or two-way ANOVA where applicable. Tukey's post hoc analysis was performed for ANOVA tests ($\alpha=0.05$; $p<0.05$ was considered statistically significant).

A differential ion mobility system suitability Lipidomix® kit from Avanti Polar Lipids (Alabaster, AL, USA) was used to determine the composition of the total major lipid classes within the samples.

Figure 11:
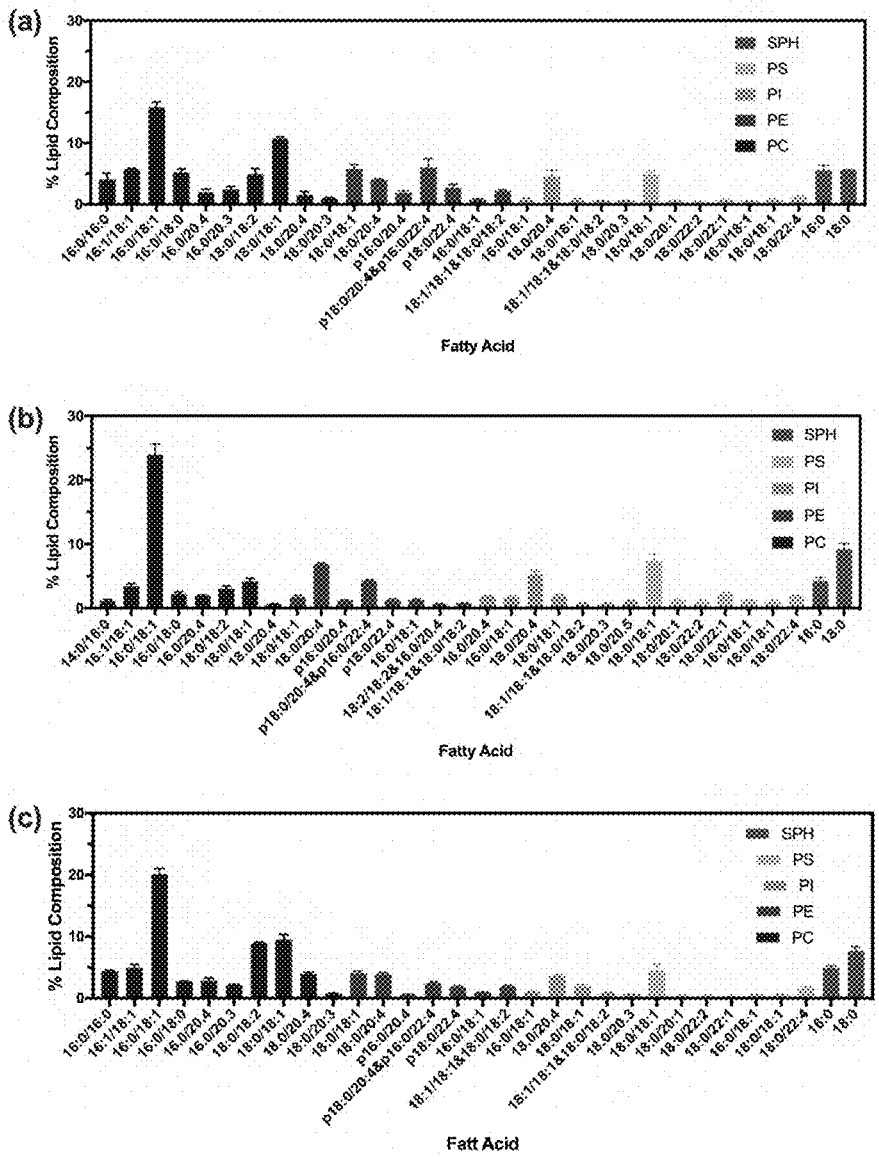
FIG. 11 is a set of bar graphs showing the full lipid composition for (a) HTR-8 cells, (b) TCL-1 cells, and (c) primary cells. Differences among the fatty acids existed within each lipid class.
Figure 12:
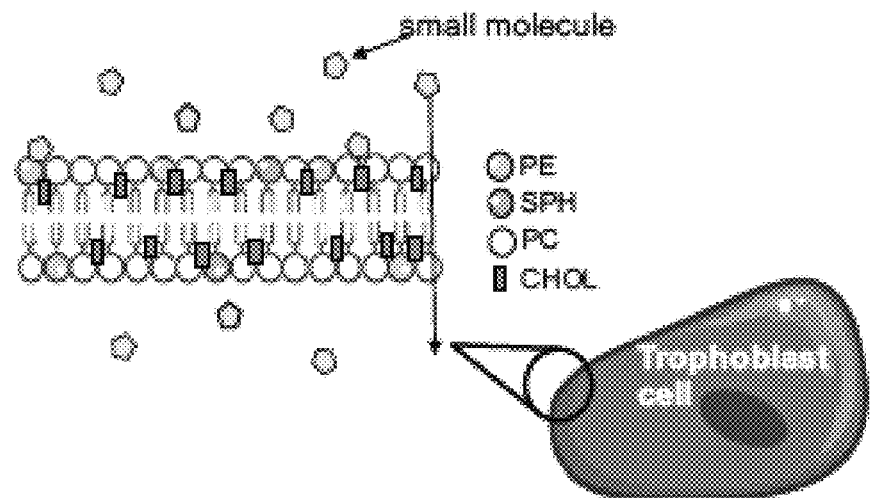
FIG. 12 is a schematic drawing of an in vitro cell-free placenta model that mimics the lipid composition of the placental cell bilayer membrane. CHOL=cholesterol, PC=phosphatidylcholine, PE=phosphatidylethanolamine, and SPH=sphingomyelin. These models provide effective tools for the rapid screening of molecular interactions with the maternal-fetal interface.
Figure 13:
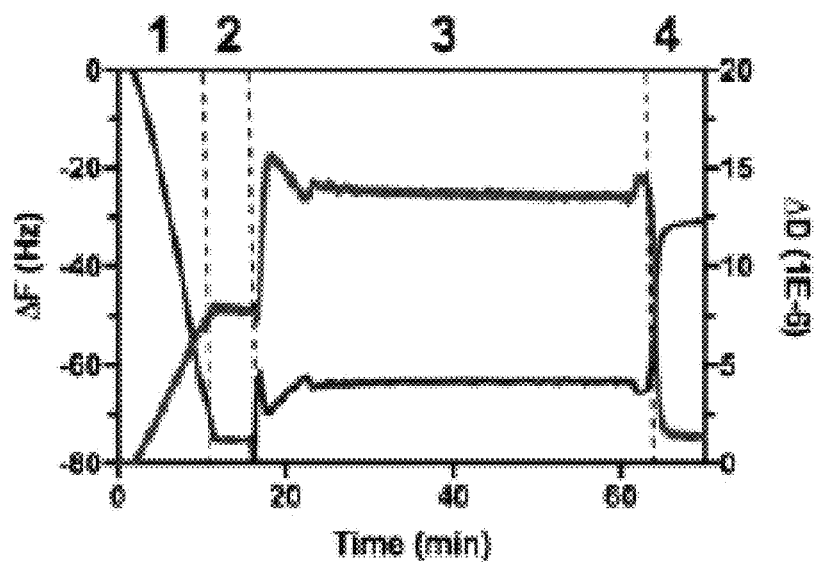
FIG. 13 is a graph showing the frequency (blue) and dissipation (red) changes during the placenta-mimicking vesicle adsorption and bilayer formation. (1) 0.3 mg/mL placental vesicles, (2) Tris NaCl, (3) peptide, (4) Tris NaCl. (n=3).

Characterization of placental lipids. Lipids extracted from HTR-8 cells, TCL-1 cells, and primary trophoblast cells were isolated and analyzed using LC-MS/MS. FIG. 1 shows the composition of the major lipid classes relative to each other. FIG. 11 shows the differences between the fatty acids within each lipid class. From these results, people having ordinary skill in the heterogeneous membranes art can observe significant differences in phosphatidylcholine (PC), phosphatidylethanolamine (PE), phosphatidylinositol (PI), and phosphatidylserine (PS) composition between HTR-8 cells, TCL-1 cells, and primary bilayers.

Placental lipids have been extracted from placental tissue and analyzed for their composition. Still, the placental lipid compositions that do exist were extracted from the term placenta, which comprises different types of cells. Huang et al., Int. J. Mol. Sci., 14 (2), 3487-3499 (2013). This EXAMPLE describes for the first-time that lipids have been extracted from HTR-8 cell, TCL-1 cell, and primary trophoblast cells. The compositions in this EXAMPLE enable a placenta bilayer mimic representative of first, third, and term trophoblast placental cells. This EXAMPLE is the first time that a lipid bilayer has been formed using a composition representing the placenta.

Example 5

Vesicle Preparation Using Synthetic Lipids and Characterization of Vesicles

Using the lipid compositions from EXAMPLE 4, The inventors developed lipid vesicles from synthetic lipids, using a dry lipid film process and extrusion through a 100 nm polycarbonate membrane. Using dynamic light scattering (DLS) and zeta ($\zeta$) potential measurements, the inventors identified the formation of uniform vesicles with low polydispersity. See FIG. 2. The $\zeta$ potentials between the different vesicles developed varied, with TCL-1 being the most negative while primary vesicles being the least negative. The TCL-1 vesicles may have the most negative charge due to the higher presence of PI and PS lipids within the composition. Also, primary trophoblast cells are the least negative vesicle, maybe due to this composition having the highest amount of PC.

The lipids 1-palmitoyl-2-oleoyl-glycero-3-phosphocholine (POPC), 1-palmitoyl-2-oleoyl-sn-glycero-3-phosphoethanolamine (POPE), 1-palmitoyl-2-oleoyl-sn-glycero-3-phospho-L-serine (POPS), L-α-phosphatidylinositol (soy) (Soy PI), and sphingomyelin (egg, chicken) (SPH) were purchased from Avanti Polar Lipids, Inc. and stored in chloroform at −20° C. The inventors dried POPC, POPE, POPS, Soy PI, and SPH at the ratio from the lipid extractions under high purity nitrogen gas obtained from TechAir (Providence, RI, USA). The dried lipid film was kept under vacuum in a chemical fume hood for at least four hours to remove excess chloroform. Dried lipids were rehydrated in a Tris sodium chloride (NaCl) buffer containing ten mM Trizma base and 100 mM NaCl, yielding a final concentration of 2.5 mg/mL placental vesicles in Tris NaCl (pH 7.8). The vesicles were then subjected to five freeze-thaw cycles and extruded ten times through an F-50 Extruder (Avestin, Ottawa, Canada), or twenty-one times through an Avanti Polar Lipids Mini Extruder (Alabaster, AL, USA) through a 100 nm pore size polycarbonate membrane (Nuclepore Track-Etch Membrane Filtration Products, Whatman, Maidstone, U.K.) to form large unilamellar vesicles (LUVs). Large unilamellar vesicles were stored under nitrogen gas at 4° C.

Vesicles were quantified for their hydrodynamic size distribution and polydispersity using dynamic light scattering (DLS) (Malvern Zetasizer ZS90 with Zetasizer 7.01 software). ζ (zeta) potential measurements were also performed using the Zetasizer and a folded capillary zeta cell (Malvern Panalytical, Westborough, MA). Vesicles were then quantified for their lipid composition by lyophilizing (FreeZone 4.5 L, Labconco, Kansas City, MO) the vesicle sample and performing LC-MS measurements as described above in EXAMPLE 4.

Example 6

Lipid Vesicle Adsorption and Placental Bilayer Formation Using a Peptide and QCM-D As shown above, a supported lipid bilayer can be developed from synthetic lipids mimicking the placenta cell membrane for adsorption and permeation studies. The inventors are developing in vitro placental bilayers using (1) synthetic lipids mimicking the composition of lipids derived from placental tissue, which have been reported, (2) cell line-extracted trophoblast lipids (including TCL-1, HTR-8, BeWo, and JEG-3 cells), and (3) placental tissue-extracted lipids. The extracted lipids are analyzed using liquid chromatography-mass spectrometry.

Vesicles adsorb to the silica surface but do not rupture spontaneously. The inventors used two methods to develop lipid bilayers. The first method was a vesicle rupture and fusion technique that takes place on a solid surface.

An α-helical peptide derived from the N-terminal amphipathic helix of the hepatitis C virus NSSA protein ruptures complex rupture complex vesicles into supported lipid bilayers, as demonstrated by Hardy et al., J. Mater. Chem., 22(37), 19506-19513 (2012); and Zan et al., J. Phys. Chem. B, 118(13), 3616-3621 (2014). The peptide sequence is described in Hardy, et al., 2012.This peptide destabilizes the outer leaflet of the vesicles, leading to rupture. Cho et al., ACS Chem. Biol., 4(12), 1061-1067 (2009). The inventors synthesized this peptide using a PS3® Peptide Synthesizer (Gyros Protein Technologies, Tucson, AZ, USA). The inventors verified the target molecular weight by liquid chromatography-mass spectrometry.

Figure 3:
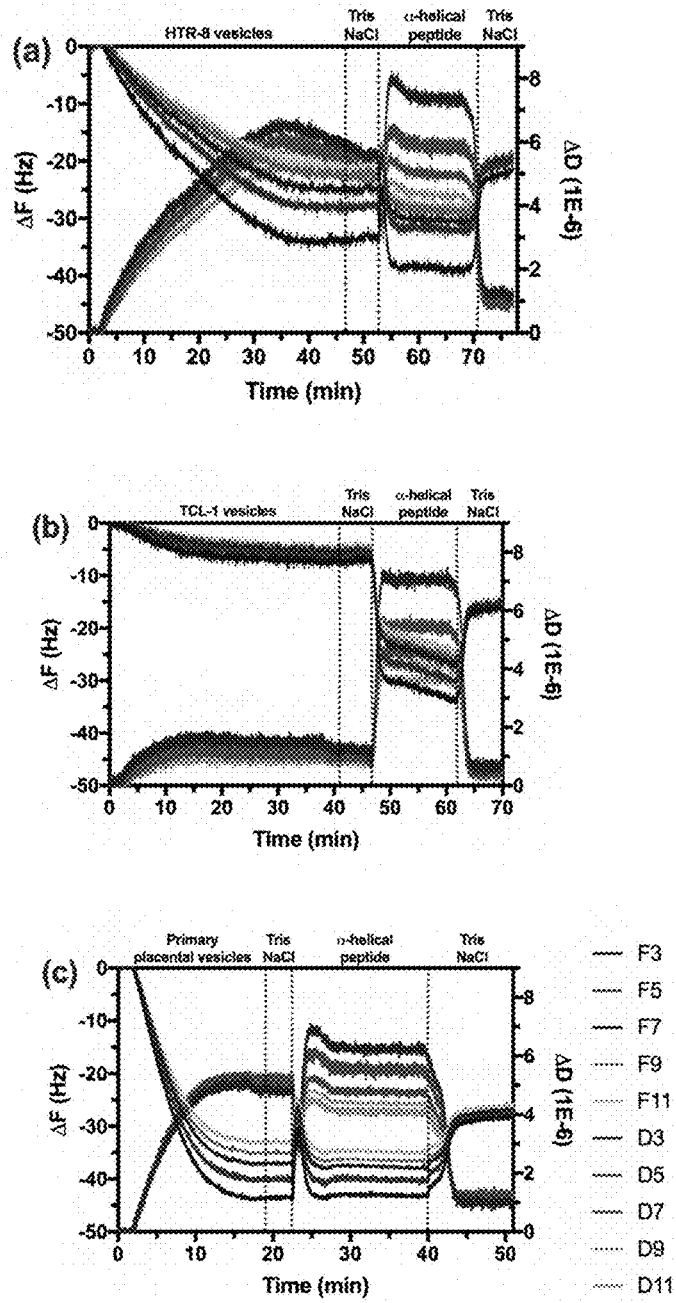
FIG. 3 shows synthetic placental bilayer formation using an α-peptide, as measured by quartz crystal microbalance with dissipation (QCM-D) plots (representative graph of n=4). These QCM-D results demonstrated the lipid bilayer formation of (A) HTR-8 cell bilayers, (B) TCL-1 cell bilayers, and (c) primary cell bilayers. Vesicles adsorb to the silica-coated substrates, as observed by the frequency change decrease and dissipation change increase. After a Tris NaCl rinse, τηε α-helical peptide ruptures the vesicles into a supported lipid bilayer. This result is observed during the final Tris NaCl rinse, where the dissipation for all bilayer types decreases. This result indicates a more rigid structure, which is typical of bilayer formation.

Using the α-helical peptide of Hardy 2012, the inventors ruptured representative vesicles into lipid bilayers by quartz crystal microbalance with dissipation (QCM-D) ($\Delta F=-30.0\pm4.4$ Hz, $\Delta D=1.3E-6\pm E-6$). See, FIG. 3. Using QCM-D, vesicles are to be adsorbed to a silica surface un-ruptured, followed by a buffer rinse, 0.3 mg/mL of the α-helical peptide, and then a final buffer rinse to remove the peptide and rupture the vesicles into a placental supported lipid bilayer. The inventors used silica-coated quartz crystals from Biolin Scientific (VaštraFrölunda, Sweden) and monitored vesicle adsorption and bilayer formation using a QCM-D E4 system from Biolin Scientific (VaštraFrölunda, Sweden).

To induce bilayer rupture, the inventors adsorbed vesicles to a silica surface. The substrates were cleaned with water, 2% w/v sodium dodecyl sulfate, and water rinse sequence, followed by drying with $N_2$ and UV/ozone treatment with a UV/ozone ProCleaner (Bioforce Nanosciences, Salt Lake City, UT, USA), before use. All studies were performed at 25° C. at a flow rate of 175 µL/min. A baseline frequency and dissipation measurement were first established in Tris NaCl for at least five minutes. HTR-8 vesicles, TCL-1 vesicles, or primary vesicles were then introduced into the QCM-D flow chamber, and the frequency and dissipation measurements were continued.

Figure 4:
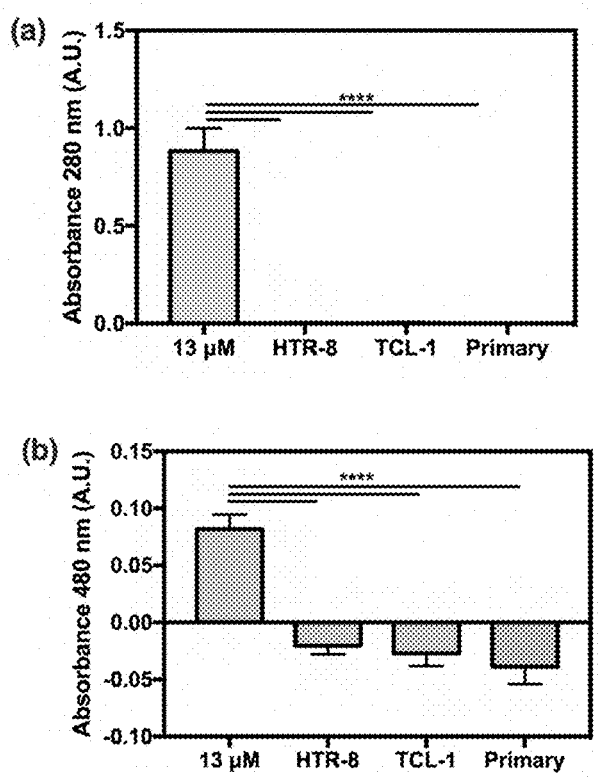
FIG. 4 is a set of bar graphs confirming the α-peptide removal after the rupture of supported lipid bilayers.
Figure 5:
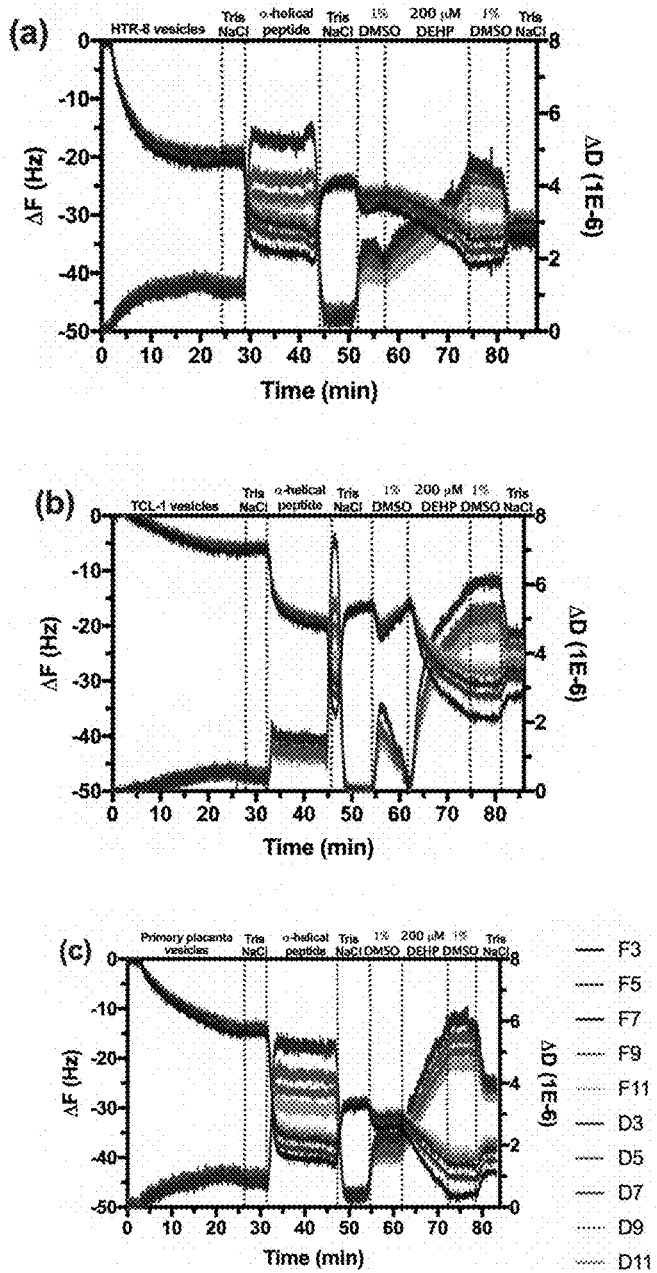
FIG. 5 is a set of quartz crystal microbalance with dissipation (QCM-D) plots showing the frequency (blue) and dissipation (red) for di-2-ethylhexyl phthalate (DEHP) interactions with HTR-8 cell, TCL-1 cell, and primary cell bilayers.
Figure 6:
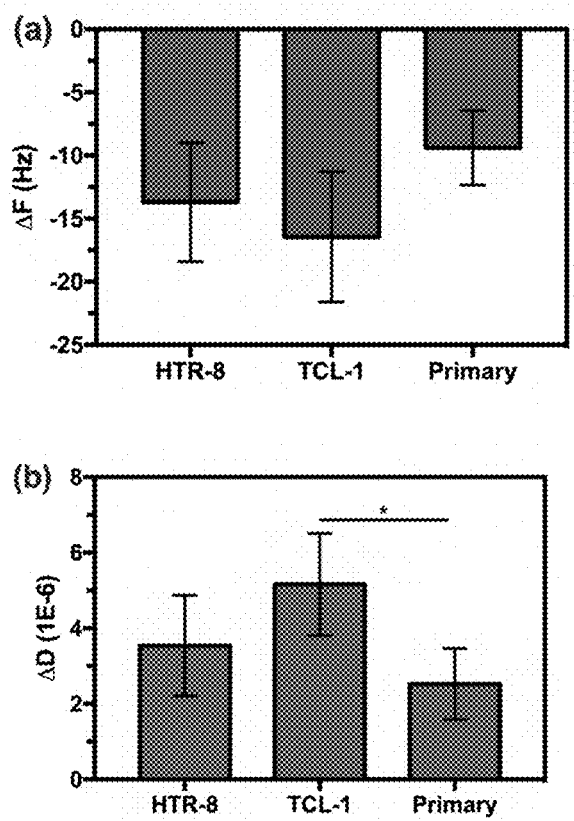
FIG. 6 is a set of bar graphs showing the frequency (blue) and dissipation (red) changes occurring due to DEHP interaction with bilayers.
Figure 7:
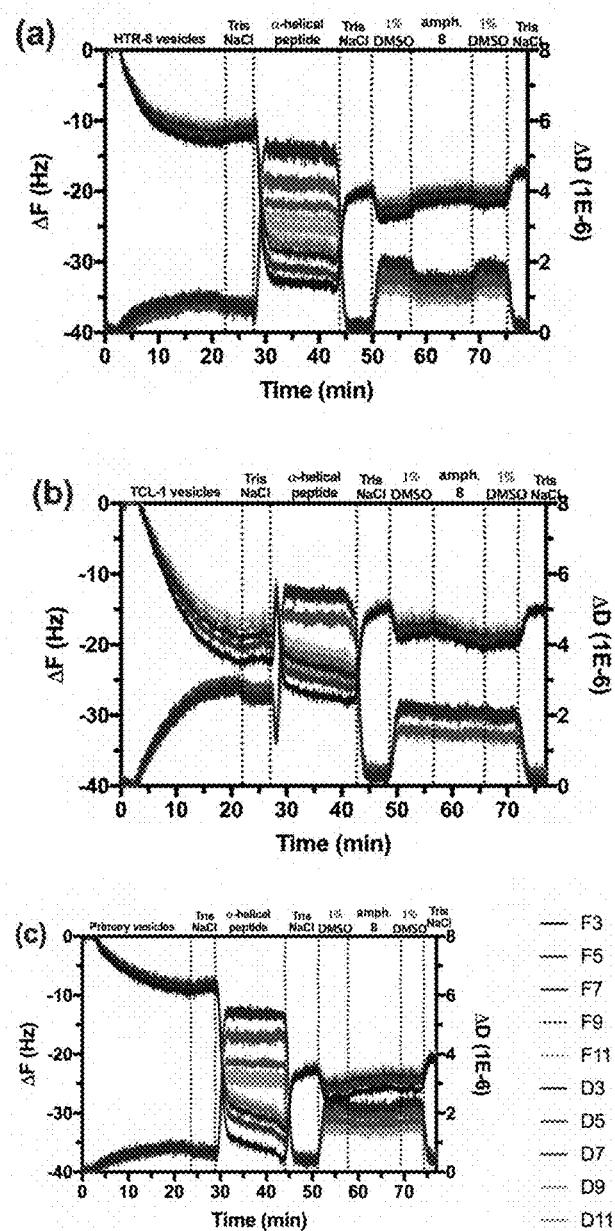
FIG. 7 is a set quartz crystal microbalance with dissipation (QCM-D) plots showing the frequency (blue) and dissipation (red) for amphotericin B with HTR-8 cell, TCL-1 cell, and primary cell bilayers.
Figure 8:
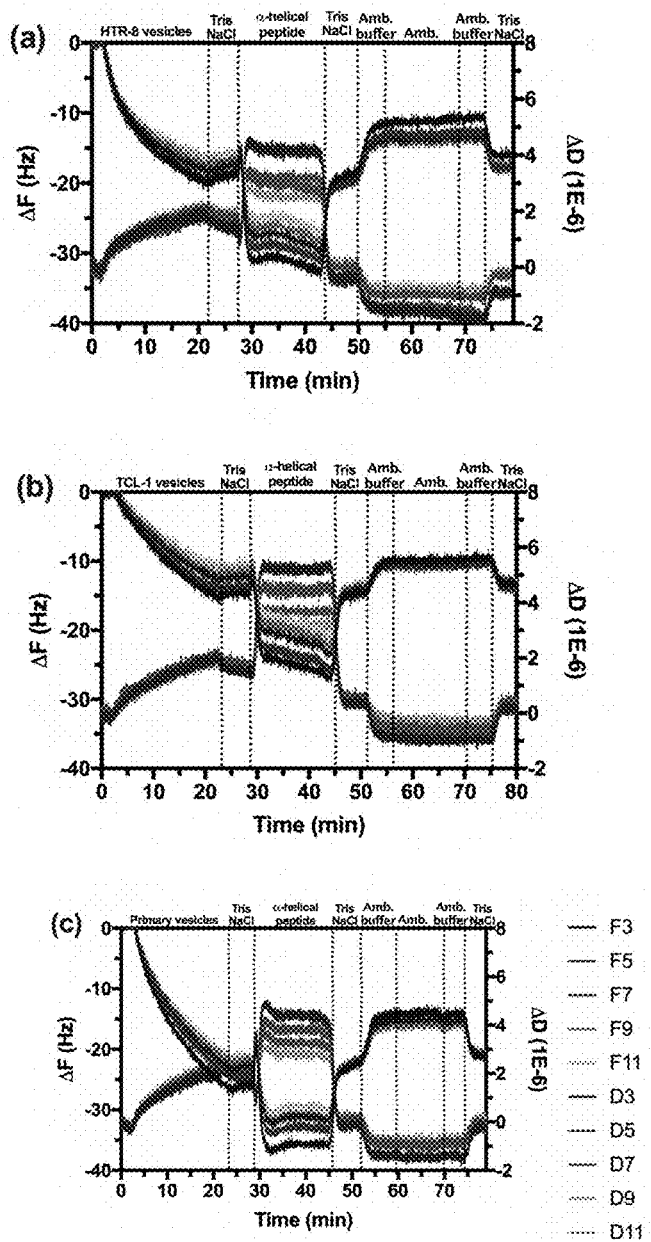
FIG. 8 is a set quartz crystal microbalance with dissipation (QCM-D) plots, showing the frequency (blue) and dissipation (red) for amBisome® with HTR-8 cell, TCL-1 cell, and primary cell bilayers.
Figure 9:
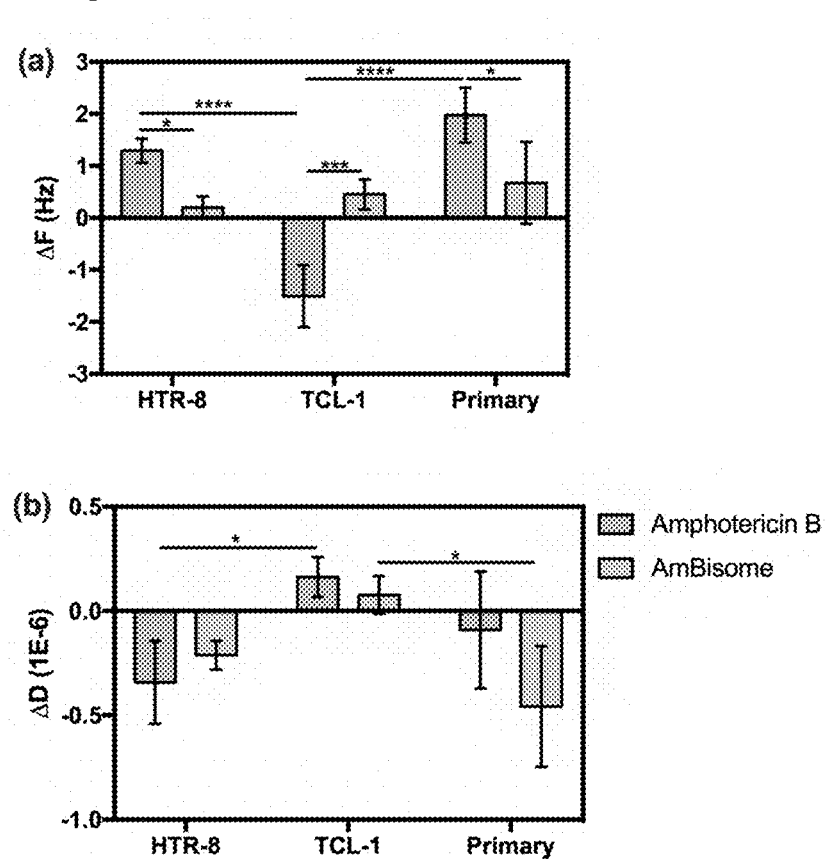
FIG. 9 is a set of bar graphs showing a comparison of frequency and dissipation changes on bilayers due to amphotericin B or amBisome®.
Figure 10:
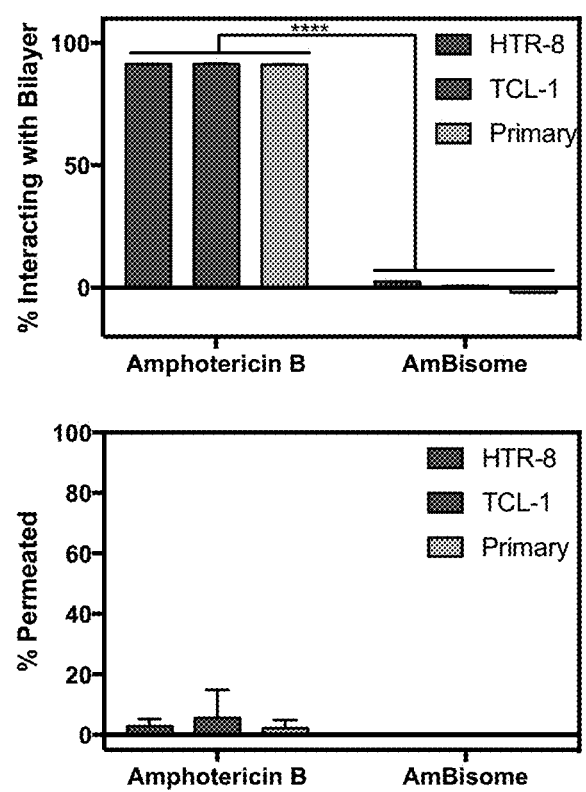
FIG. 10 is a set of bar graphs showing PAMPA results, with cell permeated and cell % interacting with bilayer using a parallel artificial membrane permeability assay (PAMPA).

The α-helical peptide of Hardy 2012 flowed over the vesicles on the silica surface and incubated on the surface for ten minutes, followed by rinsing with Tris NaCl to facilitate the vesicle rupture and removal of the peptide. The inventors confirmed the α-helical peptide was removed from the resulting bilayer by removing silica crystals from the chambers, rinsing with two mL of 2% SDS, and either running a BCA assay or detecting the peptide absorbance at 280 nm using a Pierce Quantitative Colorimetric Peptide Assay (Thermo Fisher Scientific, Waltham, MA, USA). See, FIG. 4.

Figure 2:
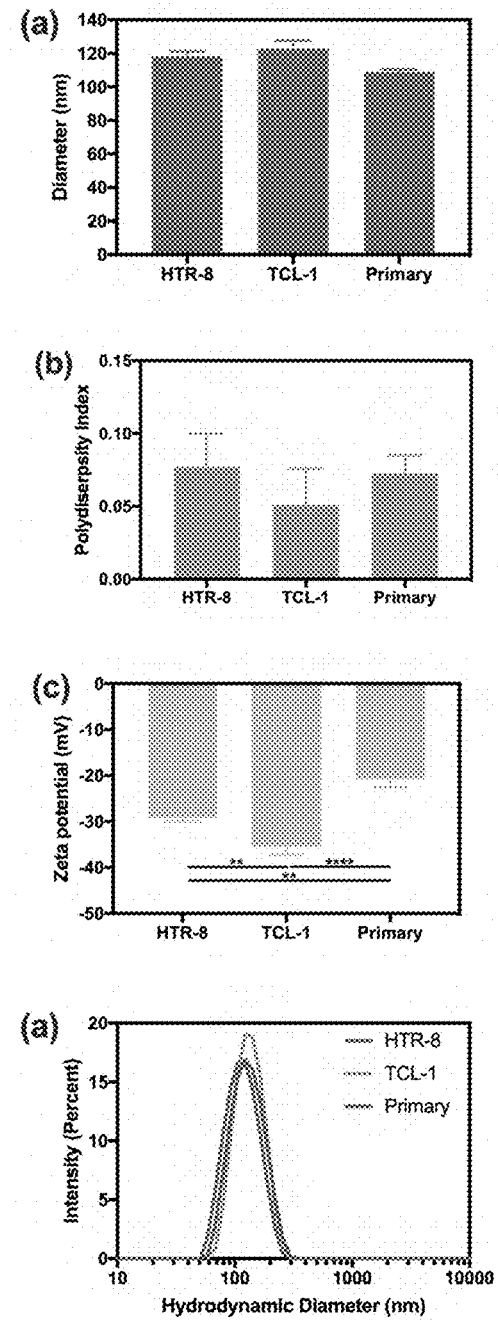
FIG. 2 is a set of bar graphs showing characterization of the size, polydispersity index (PDI), and zeta potential for HTR-8 cell lipid synthetic vesicles, TCL-1 cell lipid synthetic vesicles, and primary cell lipid synthetic vesicles. Measurements were dynamic light scattering (DLS) for HTR-8 lipid vesicles, TCL-1 lipid vesicles, and primary trophoblast lipid vesicles. (a) Diameter; (b) Polydispersity index; and (d) zeta potential. (d) Hydrodynamic size distributions for vesicles formed using HTR-8, TCL-1, and primary lipid compositions. Using dynamic light scattering (DLS) and zeta potential measurements, the inventors identified the formation of uniform vesicles with low polydispersity. The zeta potentials between the different vesicles developed were different, with TCL-1 being the most negative and primary vesicles being the least negative.

FIG. 2 shows preliminary QCM-D results of placental vesicle adsorption to a silica surface, followed by a Tris NaCl buffer rinse to stabilize the monolayer of vesicles. The inventors then introduce the α-helical peptide of Hardy 2012 to induce vesicle rupture. Previous studies have indicated that a stably supported lipid bilayer typically has an $\Delta F$ of ~25 Hz and low $\Delta D$. Hardy et al., J. Mater. Chem., 22(37), 19506-19513 (2012). The inventors also observed this $\Delta F$ and $\Delta D$ during the final buffer rinse.

First, vesicles are being developed using the dry lipid thin film method, where the lipid solution in chloroform is dried, rehydrated, and agitated using five freeze-thaw-vortex cycles. Bailey et al., Langmuir, 33(43), 11986-11997 (Sep. 26, 2017); Barenholz et al., Biochemistry, 16(12), 2806-2810 (Jun. 14, 1977). This solution is then extruded through a 100 nm polycarbonate membrane ten times. Characterization is being performed using cryo-transmission electron microscopy (cryo-TEM) and dynamic light scattering (DLS) size distribution analysis. Using quartz crystal microbalance with dissipation monitoring (QCM-D), the inventors measure frequency changes ($\Delta F$) and dissipation changes ($\Delta D$) during bilayer formation. Vesicles adsorb to the silica-coated substrates as observed by the frequency change decrease and dissipation change increase. See, FIG. 3. After the Tris NaCl rinse, the α-helical peptide is incubated to rupture the vesicles into a supported lipid bilayer. This rupture is observed at the final Tris NaCl rinse, where the dissipation for all bilayer types decreases. This result indicates a more rigid structure, which is typical of bilayer formation. This result corresponds to mass and rigidity changes, which can monitor vesicle adsorption and rupture into a supported lipid bilayer.

Example 7

Parallel Artificial Membrane Permeability Assay (PAMPA)

Using a parallel artificial permeability assay (PAMPA) with suspended lipid bilayers, polyvinylidene difluoride (PVDF) 96-well multiscreen filter plates (0.45 µcm) and transport receiver plates (Millipore-Sigma, Burlington, MA, USA), the inventors investigate DEHP, amphotericin B, and amBisome® diffusion from a donor compartment, through the porous membrane treated with lipid, to an acceptor compartment. The maximum absorbance for DEHP, amphotericin B, and amBisome® was measured using a plate reader and determined to be 280 nm, 340 nm, and 320 nm, respectively.

1,2-dioleoyl-sn-glycero-3-phosphocholine (DOPC), 1,2-dioleoyl-sn-glycero-3-phosphoethanolamine (DOPE), 1,2-dioleoyl-sn-glycero-3-phospho-L-serine (DOPS), L-α-phosphatidylinositol (soy) (Soy PI), and sphingomyelin (egg, chicken) (SPH) were solubilized in dodecane at a concentration of 20 mg/mL. The lipid classes were then mixed at the same composition quantified from the HTR-8, TCL-1, and primary trophoblast lipid extractions. Lipid mixtures (5 µL) were added to the porous PVDF membrane and immediately submerged in the donor and acceptor 1× phosphate-buffered saline (PBS) solutions to form a suspended lipid bilayer. Controls of filters introduced to dodecane only (5 µL) and treated similarly included along with untreated filters also exposed to the donor and acceptor solutions. The donor compartment was filled with 200 µL of filtered 1× PBS with 1% v/v DMSO with 200 µM DEHP and 0.1 mg/mL amphotericin B. The acceptor compartment was filled with 300 µL of filtered 1× PBS with 1% DMSO. For amBisome® (0.1 mg/ml equivalent concentration of amphotericin B), the donor compartment was filled with 200 µL of filtered 1× PBS, and the acceptor compartment was filled with 300 µL of filtered 1× PBS. The plate was rocked for two hours at 25° C. before collecting 150 µL of solution, or for sixteen hours at 25° C. before collecting 100 µL of solution, from the donor and acceptor compartments. The absorbance of DEHP, amphotericin B, and amBisome® in the solutions was measured at 280 nm, 340 nm, and 320 nm, respectively, using UV-Vis absorbance detection (Cytation 3, BioTek, Winooski, VT, USA).

Example 8

Interaction Studies With the Placental Bilayers

After the inventors accomplished bilayer formation for HTR-8 cell, TCL-1 cell, and primary cell mimetics, they performed studies to determine how pharmaceuticals and environmental toxicants interacted with these structures. For the initial interaction studies with the placental bilayer models, the inventors chose two molecules of interest.

First, the inventors investigated how di(2-ethylhexyl) phthalate (DEHP) interacts with the different placental bilayers. DEHP flowed across the bilayers at 200 µM in 1% DMSO. 1% DMSO flowed before and after the DEHP to ensure that changes observed were due to the DEHP and not a change in viscosity.

Second, the inventors are investigating the antifungal amphotericin B and its liposomal form amBisome®. During pregnancy, there is an increased vulnerability to infection. For example, vulvovaginal candidiasis occurs in up to 20% of pregnant women. Systemic fungal infections are more severe during pregnancy than at other times. Antifungal prescriptions are risky in pregnant women due to potential fetal toxicity. Pilmis et al., J. Antimicrob. Chemother., 39, 62-67 (October 2015). The placental bilayer models are useful for determining interactions of free amphotericin B as compared with amBisome®, to provide for more information on treatment strategy. Amphotericin B at 0.1 mg/mL, which is the infusion concentration, was also flowed across the bilayers to investigate the frequency and dissipation changes occurring due to this molecular interaction. Finally, the liposomal formulation of amBisome® flowed across the bilayers at an equivalent amphotericin B concentration of 0.1 mg/mL. Within a clinical vial of amBisome®, 67.8% w/w is sucrose, and 2% w/w is succinic acid. A buffer solution with equivalent amounts of sucrose and succinic acid was also flowed before and after amBisome® to account for viscosity changes between Tris NaCl and the sucrose with succinic acid buffer solution.

Example 9

A Microfluidic Device for High-Throughput Molecular Interaction Studies

The goal of this EXAMPLE 9 provides cell-free placental supported lipid bilayers translatable to a microfluidic device for high-throughput molecular interaction studies. Here the inventors test whether the placental supported lipid bilayers described above can be fabricated on a microarray with ionic current integrated monitoring. The device enables high-throughput examination of molecule-bilayer interactions. The device comprises several bilayer arrays. Measurements confirm bilayer formation and changes in the bilayer due to molecular interactions. The device operates with the same model small molecule used in the non-arrayed bilayer investigations, and permeation results are compared. The inventors expect to see the same results as analyzed with PAMPA on the individual bilayers, although with higher throughput and potentially more sensitive measurement.

Figure 14:
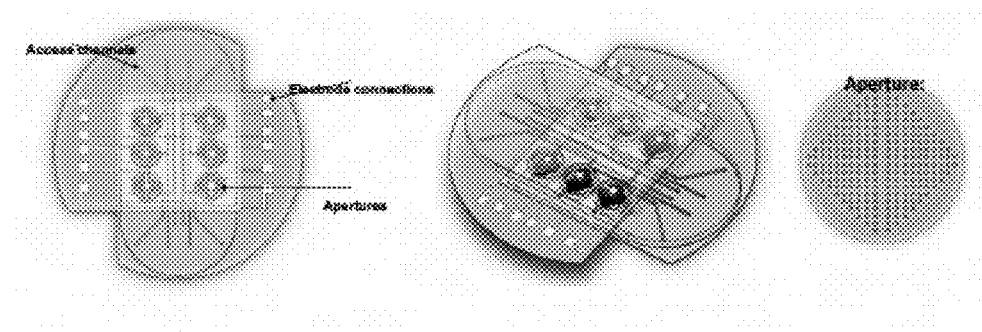
FIG. 14 is a schematic of a high-throughput placenta mimic.

Essential data is generated. Through the first phase of this research, the generated data demonstrates the formation of cell-free lipid bilayers mimicking the placenta. First, data regarding supported lipid bilayer formation using synthetic, cell-, and tissue-derived lipids will be obtained (e.g., vesicle size, bilayer thickness, special considerations for promoting lipid vesicle rupture). The proof-of-concept use of these bilayers, both as supported lipid bilayers or in PAMPA in investigating molecular interactions, are being analyzed; data gathered include $\Delta F$ and $\Delta D$ values chambers. See, FIG. 14. Apertures are formulated using soft lithography to formulate fifty µm diameter pegs, enabling suspended planar lipid bilayer membrane formation via van der Waal's interactions between the lipids and the hydrophobic pegs. All three lipid formulations explored (synthetic, cell-derived, and tissue-derived) are used. These apertures are then sandwiched between polydimethylsiloxane channel access ports. Finally, gold traces are applied using a combination of lithography and electron-beam processing to fabricate electrodes on both sides of the membrane, enabling the measurement of changes in electrical conductivity when molecules are introduced to the chamber and permeance in the presence of a model small molecule. Data comparing bilayer performance with cell line uptake and interactions are gathered. Finally, the data indicate the successful transfer of these bilayers to a high throughput device.

Next steps. A goal of this work is to develop placental bilayer mimics for high-throughput analysis of molecular interactions. The next step is using the placental bilayer mimicking systems (supported lipid bilayer and PAMPA) and the high-throughput device developed to study molecular interactions of these bilayers with pharmaceuticals, bacterial toxins, and environmental toxicants. Molecules of interest include carbofuran, di-2(ethylhexyl) phthalate (DEHP), and cholera toxin. Comparisons between interactions of these species, as detected by permeation (PAMPA), adsorption (QCM-D for supported lipid bilayers), or conductivity changes (microfluidic device) in the synthetic, cell-derived, and tissue-derived bilayers are be analyzed. These results can directly be compared to cellular outcomes using 2-D culture methods and placental organoids, which have been reported by Turco et al. Nature, 564, 263-267 (2018). Placental tissues can also be analyzed from donors with different case histories, such as pre-term birth, preeclampsia, gestational diabetes, and the like. The stability of the devices generated in different environmental conditions is also investigated to promote future use in a range of climates.

LIST OF EMBODIMENTS

Specific compositions and methods for placental lipid bilayer for cell-free molecular interaction have been described. The detailed description in this specification is illustrative and not restrictive. The detailed description in this specification is not intended to be exhaustive or to limit the disclosure to the precise form disclosed. Other equivalents and modifications besides those already described are possible without departing from the inventive concepts described in this specification, as those having skill in the art recognize. While method steps or functions are presented in a given order, alternative embodiments may perform functions in a different order, or functions may be performed substantially concurrently. Due to biological functional equivalency considerations, some changes can be made in the protein structure without affecting the biological or chemical action in kind or amount. The inventive subject matter is not to be restricted except in the spirit of the disclosure.

When interpreting the disclosure, all terms should be interpreted in the broadest possible manner consistent with the context. Unless otherwise defined, all technical and scientific terms used in this specification have the same meaning as commonly understood by one of ordinary skill in the art to which this invention belongs. This invention is not limited to the particular methodology, protocols, or reagents described in this specification and can vary in practice. The terminology used in this specification is not intended to limit the scope of the invention, which is defined solely by the claims.

All patents and publications cited throughout this specification are expressly incorporated by reference to disclose and describe the materials and methods described in such publications that might be used with the technologies described in this specification. The publications discussed are provided solely for their disclosure before the filing date. They should not be construed as an admission that the inventors are not entitled to antedate such disclosure by prior invention or for any other reason. If there is an apparent discrepancy between a previous patent or publication and the description provided in this specification, the present specification (including any definitions) and claims shall control. All statements as to the date or representation as to the contents of these documents are based on the information available to the applicants and constitute no admission as to the correctness of the dates or contents of these documents. The dates of publication provided in this specification may differ from the actual publication dates. If there is an apparent discrepancy between a publication date provided in this specification and the actual publication date provided by the publisher, the actual publication date shall control.

The terms "comprises" and "comprising" should be interpreted as referring to elements, components, or steps in a non-exclusive manner, indicating that the referenced elements, components, or steps may be present, used, or combined with other elements, components, or steps. The singular terms "a," "an," and "the" include plural referents unless context clearly indicates otherwise. Similarly, the word "or" is intended to include "and" unless the context clearly indicates otherwise. The abbreviation "e.g." is used to indicate a non-limiting example and is synonymous with the term "for example."

When a range of values is provided, each intervening value, to the tenth of the unit of the lower limit, unless the context dictates otherwise, between the upper and lower limit of that range and any other stated or intervening value in that range of values.

Some embodiments of the technology described can be defined according to the following numbered paragraphs:

1. An in vitro cell-free placenta model that mimics the lipid composition of the placental cell membrane.
2. An in vitro cell-free placenta model that mimics the lipid composition of the placental cell membrane at different times during pregnancy.
3. An in vitro cell-free placenta model that mimics the lipid composition of the placental cell membrane at the first-trimester stage of pregnancy.
4. An in vitro cell-free placenta model that mimics the lipid composition of the placental cell membrane at the third-trimester stage of pregnancy.
5. An in vitro cell-free placenta model that mimics the lipid composition of the placental cell membrane at the full-term stage of pregnancy.
6. An in vitro cell-free placenta model that comprises phosphatidylcholine (PC), phosphoethanolamine (PE), phosphatidylinositol (PI), phosphatidylserine (PS), and sphingomyelin (SPH).
7. An in vitro cell-free placenta model that consists of phosphatidylcholine (PC), phosphoethanolamine (PE), phosphatidylinositol (PI), phosphatidylserine (PS), and sphingomyelin (SPH).
8. An in vitro cell-free placenta model that comprises one or more lipids selected from the group consisting of phosphatidylcholine (PC), phosphoethanolamine (PE), phosphatidylinositol (PI), phosphatidylserine (PS), and sphingomyelin (SPH).
8. An in vitro cell-free placenta model that consists of one or more lipids selected from the group consisting of phosphatidylcholine (PC), phosphoethanolamine (PE), phosphatidylinositol (PI), phosphatidylserine (PS), and sphingomyelin (SPH).
9. An in vitro cell-free placenta model that mimics the lipid composition of the placental cell membrane and provides for the rapid screening of molecular-scale interactions of molecules with the maternal-fetal interface.
10. An in vitro cell-free placenta model that mimics the lipid composition of the placental cell membrane, comprising synthetic lipid vesicles, a synthetic lipid bilayer, or both synthetic lipid vesicles and synthetic lipid bilayer; and comprising the most abundant lipids in the placenta.
11. An in vitro cell-free placenta model that mimics the lipid composition of the placental cell membrane, wherein the model is a unilipid or a multi-lipid.
12. An in vitro cell-free placenta model that mimics the lipid composition of the placental cell membrane, wherein the model is a phosphatidylcholine unilipid.
13. An in vitro cell-free placenta model that mimics the lipid composition of the placental cell membrane, comprising trophoblast cell line-extracted lipids.
14. An in vitro cell-free placenta model that mimics the lipid composition of the placental cell membrane, comprising trophoblast cell line-extracted lipids from cells representative of first-trimester trophoblast cells.

We claim:

1. An in vitro, cell-free, human placenta model comprising:

1) a membrane supporting a lipid bilayer, the bilayer including a composition of synthetic lipids and/or natural lipids representing a ratio of lipids measured from a lipid extraction from a human placental cell membrane at a first, second, third trimester, or a term pregnancy;
   2) a donor compartment disposed on one side of the bilayer; said compartment holding a test compound in contact with the one side of the bilayer; and
   3) a detector for detecting at least one of the test compound's permeation through the bilayer, the test compound's adsorption on the bilayer, or a conductivity effect on the bilayer due to the contact with the test compound; said detecting during and/or after a time that the test compound is in contact with the bilayer;
   wherein the in vitro placenta model is capable of simulating the test compound's permeation through, the test compound's adsorption on, or the test compound's conductivity effects on an in vivo human placenta because the ratio of lipids of the in vitro bilayer is measured from the lipid extraction from the human placental cell membrane.

2. The in vitro, cell-free placenta model of claim 1, wherein the lipid bilayer is further comprising:
   synthetic lipid vesicles or both synthetic lipid vesicles and synthetic lipid bilayer; and
   is further comprising lipids that are the most abundant measured from the human placenta including phosphatidylcholine (PC), phosphoethanolamine (PE), phosphatidylinositol (PI), phosphatidylserine (PS), sphingomyelin (SPH), or a combination thereof.

3. The in vitro, cell-free placenta model of claim 1, wherein the model further comprises at least in a portion of the bilayer a single lipid (a unilipid) or a combination of multiple lipids (a multi-lipid).

4. The in vitro, cell-free placenta model of claim 1, comprising human trophoblast cell line-extracted lipids.

5. The in vitro, cell-free placenta model of claim 1, comprising human placenta tissue-extracted lipids.

6. The in vitro, cell-free placenta model of claim 1, further comprising an acceptor compartment configured on the opposite side of the bilayer as the donor compartment, such that the model is capable of simulating the test compound's permeation through an in vivo human placenta by the test compound's permeation from the donor compartment through the in vitro bilayer and into the acceptor compartment.

7. The in vitro, cell-free placenta model of claim 1, wherein the detector comprises a quartz crystal microbalance operative to provide frequency changes ($\Delta F$) and/or dissipation changes ($\Delta D$), (QCM-D), disposed on a side of the bilayer, such that the model is capable of simulating the test compound's adsorption on or into an in vivo human placenta by a QCM-D monitoring of a viscoelasticity of the in vitro bilayer.

8. The in vitro, cell-free placenta model of claim 1, further comprising wherein the detector comprises electrodes on both sides of the in vitro bilayer, said electrodes capable of providing a measurement of changes in electrical conductivity after the test compound is introduced into the donor chamber.

9. The in vitro, cell-free placenta model of claim 1, wherein the detector comprises a UV-Vis absorbance detector, a mass spectrometry detector, a conductivity detector, a colorimetric detector, a fluorescence detector, or a combination thereof.

15. An in vitro cell-free placenta model that mimics the lipid composition of the placental cell membrane, comprising trophoblast cell line-extracted lipids from HTR-8 cells.

16. An in vitro cell-free placenta model that mimics the lipid composition of the placental cell membrane, comprising trophoblast cell line-extracted lipids from cells representative of third-trimester trophoblast cells.

17. An in vitro cell-free placenta model that mimics the lipid composition of the placental cell membrane, comprising trophoblast cell line-extracted lipids from TCL-1 cells.

18. An in vitro cell-free placenta model that mimics the lipid composition of the placental cell membrane, comprising trophoblast cell line-extracted lipids from BeWo cells.

19. An in vitro cell-free placenta model that mimics the lipid composition of the placental cell membrane, comprising trophoblast cell line-extracted lipids from JEG-3 cells.

20. An in vitro cell-free placenta model that mimics the lipid composition of the placental cell membrane, comprising trophoblast cell line-extracted lipids from primary trophoblast cells.

21. An in vitro cell-free placenta model that mimics the lipid composition of the placental cell membrane, comprising placenta tissue-extracted lipids.

22. A device for the rapid screening of molecular-scale interactions of molecules with the maternal-fetal interface that mimics the lipid composition of the placental cell membrane.

23. A method for testing compounds for interactions with the placenta at the molecular scale.

24. A method for testing compounds for interactions with the placenta at the molecular scale, where the compounds are pharmaceuticals.

25. A method for testing compounds for interactions with the placenta at the molecular scale, where the compounds are folic acid.

26. A method for testing compounds for interactions with the placenta at the molecular scale, where the compounds are amphotericin B.

27. A method for testing compounds for interactions with the placenta at the molecular scale, where the compounds are amBisome®.

28. A method for testing compounds for interactions with the placenta at the molecular scale, where the compounds are environmental toxicants.

29. A method for testing compounds for interactions with the placenta at the molecular scale, where the compounds are phthalates.

30. A method for testing compounds for interactions with the placenta at the molecular scale, where the compounds are di(2-ethylhexyl) phthalate (DEHP).

31. A method for testing compounds for interactions with the placenta at the molecular scale, where the compounds carbofuran.

32. A method for testing compounds for interactions with the placenta at the molecular scale, where the compounds are toxins.

33. A method for testing compounds for interactions with the placenta at the molecular scale, where the compounds are cholera toxin.

10. The in vitro, cell-free placenta model of claim 1, wherein the membrane supporting the lipid bilayer comprises a polymer and/or placental collagen.

\* \* \* \* \*